(12) United States Patent
Carson et al.

(10) Patent No.: US 6,897,319 B2
(45) Date of Patent: May 24, 2005

(54) USEFUL AROYL PYRROLE HETEROARYL METHANONES AND METHANOLS

(75) Inventors: John R. Carson, Norristown, PA (US); Ellen E. Codd, Blue Bell, PA (US); Philip M. Pitis, North Wales, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 47 days.

(21) Appl. No.: 10/315,585

(22) Filed: Dec. 10, 2002

(65) Prior Publication Data

US 2003/0181481 A1 Sep. 25, 2003

Related U.S. Application Data

(60) Provisional application No. 60/343,768, filed on Dec. 27, 2001.

(51) Int. Cl.$^7$ ............... A61K 31/4439; A61K 31/4178; C07D 401/06; C07D 401/14; C07D 403/06
(52) U.S. Cl. ................ 546/279.1; 546/146; 546/168; 546/268.1; 546/256; 548/314.7; 548/314.1; 548/517; 548/518; 548/527; 548/539; 514/343; 514/397; 514/422; 514/314; 514/307
(58) Field of Search .......................... 546/279.1, 168, 546/146, 256; 548/314.7, 517, 518, 527, 539; 514/343, 397, 422, 314, 307

(56) References Cited

U.S. PATENT DOCUMENTS

| | | | |
|---|---|---|---|
| 6,051,583 A | 4/2000 | Grauert et al. | |
| 6,169,116 B1 | 1/2001 | Swoboda | |
| 6,172,085 B1 | 1/2001 | Ohkawa et al. | |
| 6,191,142 B1 * | 2/2001 | Carson et al. ............. | 514/307 |
| 6,255,307 B1 | 7/2001 | Cox et al. | |
| 6,262,078 B1 | 7/2001 | Loughhead et al. | |
| 6,265,405 B1 | 7/2001 | Cox et al. | |
| 6,281,211 B1 | 8/2001 | Cai et al. | |
| 6,288,123 B1 | 9/2001 | Goldin et al. | |
| 6,288,278 B1 | 9/2001 | Sundermann et al. | |

FOREIGN PATENT DOCUMENTS

| | | |
|---|---|---|
| WO | WO 00/02865 A1 | 1/2000 |
| WO | WO 0048684 | 8/2000 |
| WO | WO 00/61231 A3 | 10/2000 |
| WO | WO 01/23570 A3 | 4/2001 |

OTHER PUBLICATIONS

Roufos et al. J. Med. Chem. 1996, 39:1514–1520.*
Zakrzewska et al. Journal of Biomolecular Structure & Dynamics. 1988, 5(5): 1043–1058.*
Tamura et al., "Focal Cerebral Ischaermia in the Rat: 1. Description of Technique and Early Neuropathological Consequences Following Middle Cerebral Artery Occlusion." *J. Cereb. Blood Flow Metabolism*, 1981, 53–60, vol. t.
Postma S.W. &.Catterall W.A, "Inhibition of Binding of [3H] Batrachotoxinin A 20–α–Benzoate to Sodium Channels by Local Anesthetics." *Molecular Pharmacology*, 1984, 219–227, vol. 25.
Leach M. J. et al., "BW619C89, a Glutamate Release Inhibitor, Protects Against Focal Cerebral Ischemic Damage." *Stroke*. 1993, 1063–1067, vol. 24.
Brown G.B., "3H–Batrochotoxinin–A Benzoate Binding to Voltage–Sensitive Sodium Channels: Inhibition by the Channel Blockers Tetrodotoxin and Saxitoxin." *Journal of Neuroscience*, 1986, 2064–2070, vol. 6.
Sauter A. and Rudin M., "Calcium Antagonists Reduce the Extent of Infarction in Rat Middle Cerebral Artery Occlusion Model as Determined by Quantitative Magnetic Resonance Imaging." *Stroke*. 1986, 1228–1234, vol. 17
Courtney K.R. and Stricharz G.R., "Structural Elements which Determine Local Anesthetic Activity" *Handbook of Experimental Pharmacology*, Springer–Verlag, New–York, 1987, 55–94, vol. 81, Ch.3.
Catterall W.A., "Common modes of drug action on Na+ channels: local anesthetics, antiarrhythmics and anticonvulsants" *Trends in Pharmacological Sciences*. 1987, 57–65, vol. 8.
Bennet G.J. and Xie Y.K., "A peripheral mononeuropathy in rat that produces disorders of pain sensation like those seen in man." *Pain*, 1988, 87–107, vol. 33.
Villauneva S., Frenz P., Dragnic Y and Orrego F., "Veratridine–induced release of endogenous glutamate from rat brain cortex slices: a reappraisal of the role of calcium." *Brain Research*, 1988, 377–380, vol. 461.
Rogawski M.A and Porter R.J. "Antiepileptic Drugs: Pharmacological Mechanisms and Clinical Efficacy with Consideration of Promising Developmental Stage Compounds." *Pharmacological Reviews*, 1990, 223–286, vol. 42.
Kim S.H. & Chung J.M., "An experimental model for peripheral neuropathy produced by segmental spinal nerve ligation in the rat. " *Pain*, 1992, 355–363, vol. 50.
Pschorn U. and Carter A.J., "The influence of Repeated Doses, Route and Time of Administation on the Neuroprotective Effects of BIII 277 CL in a Rat Model of Focal Cerebral Ischemia." *J. Stroke Cerebrovascular Diseases*. 1998, 93–99, vol. 6.
Yoon, Dao–Wi, et al. "Synthesis and NMR Studies of Core–Modified , N–Confused Porphyrine Possessing Alkyl Groups at the Rim Nitrogen", Bulletin of the Korean Chemical Society (2000), 21(6), pp. 618–622.
Barbero, Margharita et al., "Pentastomic Hetoroaromatic Cations, 18. Acylation of Pyrrole and N–Methylpyrrole with 1,3–Benzoxathiolium Tetrafluoroborates. A high–Yield Method for the Synthesis of Diacylpyrroles", Journal of Organic Chemistry (1938), 53(10), pp. 2245–2260.
PCT International Search Report dated Apr. 7, 2003 for PCT Appln. No. PCT/US 02/39487 which relates toAppl. No. 10/315,585.

* cited by examiner

*Primary Examiner*—Evelyn Mei Huang

(57) ABSTRACT

This invention is directed to aroyl pyrrole heteroaryl methanone and methanol compounds pharmaceutically useful as agents for treating or modulating a central nervous system disorder and methods for treating or modulating a central nervous system disorder.

9 Claims, No Drawings

USEFUL AROYL PYRROLE HETEROARYL METHANONES AND METHANOLS

This application claims priority to and the benefit of U.S. Provisional Application No. 60/343,768 filed Dec. 27, 2001.

FIELD OF THE INVENTION

This invention relates to compounds useful as agents for treating or modulating a central nervous system disorder. More particularly, this invention relates to aroyl pyrrole heteroaryl methanone and methanol compounds useful as agents for treating or modulating a central nervous system disorder.

BACKGROUND OF THE INVENTION

The conditions grouped under the term "central nervous system disorder" constitute an area of continuing medical need. Such conditions include those disorders associated with neuropathic pain, inflammatory pain, inflammation-related pain or epilepsy.

Sodium channels have been suggested to play a role in (and sodium channel blockers to be useful in treating) many disorders of the central nervous system (Madge, D., Sodium Channels: Recent Developments and Therapeutic Potential, *Annual Reports in Medicinal Chemistry,* 1998, 33, 51–60, 56). The majority of the compounds studied to date show some potential in more than one of these disorders; very few compounds with selective anticonvulsant, analgesic or neuroprotective activity have been identified (Madge, D., p 56).

In the past few years a much better understanding of sodium channels and drugs interacting with them has been developed (Anger, T., Madge, D., Mulla M. and Riddall, D., Medicinal Chemistry of Neuronal Voltage-Gated Sodium Channel Blockers, *Journal of Medicinal Chemistry,* 2001, 44(2), 115–137). It has become clear that a number of drugs having an unknown mechanism of action actually act by modulating sodium channel conductance, including local anesthetics, class I antiarrhythmics and anticonvulsants (Anger, T., et al., p 123). Neuronal sodium channel blockers have found application with their use in the treatment of epilepsy (phenytoin and carbamazepine, long used as anticonvulsants but without a clear understanding of their mechanism of action), neuroprotection (as a result of ischemic stroke and other brain trauma), preventing neurodegeneration (such as in the treatment of amyotrophic lateral sclerosis by, primarily, sodium channel blockage) and in reducing neuropathic pain (as a result of trigeminal neuralgia, diabetic neuropathy, post-herpetic neuralgia, neuroma pain and phantom limb syndrome) (Anger, T., et al., pp 124, 126, 129).

Neuropathic pain and other chronic and debilitating condition-associated pain syndromes are all associated with changes in neuronal excitability (Brau M. E., et al, Effect of drugs used for neuropathic pain management on tetrodotoxin-resistant Na(+) currents in rat sensory neurons, *Anesthesiology,* 2001, January, 94(1), 137–44; Siddall P. J. and Loeser J. D., Pain following spinal cord injury, *Spinal Cord,* 2001, February, 39(2), 63–73; Kontinen V. K., et al, Electrophysiologic evidence for increased endogenous gabanergic but not glycinergic inhibitory tone in the rat spinal nerve ligation model of neuropathy, *Anesthesiology,* 2001, February, 94(2), 333–9).

Various anti-epileptic drugs (AEDs) that stabilize neuronal excitability are effective in neuropathic pain (Johannessen C. U., Mechanisms of action of valproate: a commentatory, *Neurochem. Int.,* 2000, August–September, 37(2–3), 103–110 and Magnus L., Nonepileptic uses of gabapentin, *Epilepsia,* 1999, 40 Suppl 6, S66-72; Nadin Attal, et al., Effects of Gabapentin on the Different Components of Peripheral and Central Neuropathic Pain Syndromes: A Pilot Study, *Fr. Eur. Neurol.* 1998, 40(4), 191–200.

In particular, neuropathic pain is defined as pain caused by aberrant somatosensory processing in the peripheral or central nervous system and includes neuropathic pain resulting from chronic or debilitating conditions (such as painful diabetic peripheral neuropathy, post-herpetic neuralgia, trigeminal neuralgia, post-stroke pain, multiple sclerosis-associated pain, neuropathies-associated pain (such as in idiopathic or post-traumatic neuropathy and mononeuritis), HIV-associated neuropathic pain, cancer-associated neuropathic pain, carpal tunnel-associated neuropathic pain, spinal cord injury-associated pain, complex regional pain syndrome, fibromyalgia-associated neuropathic pain, lumbar and cervical pain, reflex sympathetic dystrophy, phantom limb syndrome and other chronic and debilitating condition-associated pain syndromes), sympathetically maintained pain or cluster and migraine headache-associated pain; pain associated with cancer, fibromyalgia, back disorders or migraine and chronic headache, adiposis dolorosa and burn pain, central pain conditions following stroke, thalamic lesions or multiple sclerosis or pain resulting from damage to the peripheral or central nervous system (after amputation, paraplegia, herpes or as a result of diabetic polyneuropathy).

An increase in sodium channel expression or activity is observed in several animal models of inflammatory pain. Expression of α-SNS mRNA and tetrodotoxin-resistant sodium current in small DRG neurons increased following injection of carrageenan into the plantar surface of the rat hindpaw (Tanaka M., *NeuroReport,* 1998, 9, 967–972). Similarly, the induction of chronic inflammation with the injection of Complete Freund's Adjuvant was followed by the development of inflammatory thermal hypersensitivity and increased sodium channel staining (Gould H. J., et al., *Brain Res.,* 1998, 802 (1), 69–74; Gould H. J., et al., *Brain Res.,* 1999, 824, 296–299). Antisense (but not sense or missense) to the PN3 sodium channel prevented the development of mechanical flexion reflex hyperalgesia following the administration of the inflammatory agent $PGE_2$ (Khasar S. G., et al., *Neurosci. Lrs.,* 1998, 256, 17–20).

Patent references describe compounds as sodium channel modulators or antagonists for use in treating or modulating central nervous system disorders in a number of in vitro and in vivo models.

U.S. Pat. No. 6,288,278 describes 3-amino-3-arylpropan-1-ol derivatives as sodium channel blockers in a BTX-binding assay (S. W. Postma & W. A. Catterall, Mol. Pharmacol., 1984 25, 219–227) and methods for use as local anesthetic, antiarrhythmic, antiemetic and nootropic (neurotropic) agents and as agents for the treatment/therapy of cardiovascular diseases, urinary incontinence, diarrhea, pruritus, alcohol or drug dependency and inflammation.

U.S. Pat. No. 6,288,123 describes disubstituted guanidine compounds as modulators or inhibitors for release of neurotransmitters such as glutamate from ischemic neuronal cells by blocking presynaptic calcium and/or sodium channels in an inhibition of glutamate release assay, in an inhibition of $^{45}Ca$ uptake through presynaptic calcium channels assay, in an inhibition of $^{45}Ca$ uptake through L-type (dihydropyridine-sensitive) calcium channels assay, in an inhibition of $[^{14}C]$-guanidinium uptake through Type II neuronal voltage-activated sodium channels assay, in an in vivo anticonvulsant/audiogenic seizures D6A/2 mouse model and methods for use in the treatment and/or prophylaxis of neurological conditions such as epilepsy, neurodegenerative conditions and diseases (such as Parkinson's disease, Huntington's disease, Amyotrophic Lateral Sclerosis, Alzheimer's disease, Down's Syndrome, Korsakoff's disease, olivopontocerebellar atrophy, HIV-induced dementia and blindness or multi-infarct dementia) and nerve cell death (as a result of hypoxia, hypoglycemia, brain or spinal chord ischemia, brain or spinal chord trauma or global cerebral ischemia (as a result of stroke, heart attack, drowning or carbon monoxide poisoning)); for use in the treatment of hypertension, cardiac arrhythmias or angina pectoris, endocrine disorders (such as acromegaly and diabetes insipidus) and chronic pain (including use as a local anesthetic); and, for use in the treatment of diseases in which the pathophysiology of the disorder involves excessive or otherwise inappropriate (e.g., hypersecretory) cellular secretion (e.g., secretion of an endogenous substance such as a catecholamine, a hormone or a growth factor).

U.S. Pat. No. 6,281,211 describes semicarbazide compounds as sodium channel blockers in a dissociated hippocampal neuron electrophysiological assay, in a neuronal voltage-dependent in a rat forebrain membrane assay, in HEK-293 cells stably expressing hSkM 1 sodium channels, in a [$^3$H]BTX-B assay and in a mouse maximal electroshock-induced seizure (MES) model and methods for treating, preventing or ameliorating neuronal loss (associated with stroke, global and focal ischemia, CNS trauma, hypoglycemia, surgery and spinal cord trauma), for the treatment or prevention of neurodegenerative conditions (such as Alzheimer's disease, amyotrophic lateral sclerosis (ALS), Parkinson's disease, anxiety, convulsions, glaucoma, migraine headache and muscle spasm), as antimanic depressants, as local anesthetics, as antiarrhythmics, as anticonvulsants, as agents for the treatment or prevention of diabetic neuropathy and for the treatment of pain (acute, chronic and surgical pain, neuropathic pain and migraine headache).

U.S. Pat. No. 6,265,405 describes 5-amino triazine derivatives as sodium channel blockers in a whole-cell (recombinant human brain type IIA Na$^+$ channel expressed in Chinese hamster ovary cells) voltage-clamp assay, as anticonvulsants in a rat MES model and a mouse pentylenetetrazol infusion test, as agents for treating acute hyperalgesia and inflammation in a rat carrageenan paw model, as a neuroprotective agent in a MPTP-induced neurotoxicity model for Parkinson's disease and methods for treating epilepsy (including simple partial seizures, complex partial seizures, secondary generalised seizures and generalized seizures (further including absence seizures, myoclonic seizures, clonic seizures, tonic seizures, tonic clonic seizures and atonic seizures), bipolar disorder (alternatively known as manic depression; including Type I or II) and unipolar depression; for treating or preventing acute pain (musculoskeletal, post operative and surgical pain), chronic pain (inflammatory pain (from rheumatoid arthritis and osteoarthritis), neuropathic pain (from post herpetic neuralgia, trigeminal neuralgia and sympathetically maintained pain) and pain associated with cancer, fibromyalgia and migraine associated pain; for treating tinnitus, functional bowel disorders (non-ulcer dyspepsia, non-cardiac chest pain and irritable bowel syndrome) and neurodegenerative diseases (Alzheimer's disease, ALS, motor neuron disease, Parkinson's disease, muscular sclerosis, macular degeneration and glaucoma), for neuroprotection (treating neurodegeneration following stroke, cardiac arrest, pulmonary bypass, traumatic brain injury and spinal cord injury) and for preventing or reducing dependence/tolerance/ reverse tolerance to a dependence-inducing agent (such as opioids, CNS depressants, psychostimulants and nicotine).

U.S. Pat. No. 6,262,078 describes phenoxymethyl piperidine derivatives as sodium channel blockers in an in vitro rat vagus nerve assay (Kourtney and Stricharz, *Local Anesthetics*, Springer-Verlag, New York, 1987) and as agents for the treatment of neuropathic pain in an in vivo rat mechanical allodynia model (Kim and Chung, *Pain*, 1992, 50:355–363), in an in vivo rat acute and chronic cold allodynia, unilateral mononeuropathy, Chronic Constriction Injury model (Bennet and Xie, *Pain*, 1988, 33:87–107), in an in vivo rat mechanical hyperalgesia model (Bennet and Xie, *Pain*, 1988, 33:87–107) and in an in vivo rat thermal hyperalgesia model and methods for treating peripheral neuropathies (trigeminal neuralgia, postherpetic neuralgia, diabetic neuropathy, glossopharyngeal neuralgia, lumbar and cervical radiculopathies, reflex sympathetic dystrophy and causalgia), neuropathy secondary to metastatic infiltration, adiposis dolorosa and burn pain and central pain conditions following stroke, thalamic lesions and multiple sclerosis.

U.S. Pat. No. 6,255,307 describes a class of phenyl pyrazine derivatives as sodium channel blockers and methods for treating epilepsy (including simple partial seizures, complex partial seizures, secondary generalised seizures and generalized seizures (further including absence seizures, myoclonic seizures, clonic seizures, tonic seizures, tonic clonic seizures and atonic seizures), bipolar disorder (alternatively known as manic depression; including Type I or II) and unipolar depression; for treating or preventing acute pain (musculoskeletal, post operative and surgical pain), chronic pain (inflammatory pain (from rheumatoid arthritis and osteoarthritis), neuropathic pain (from post herpetic neuralgia, trigeminal neuralgia and sympathetically maintained pain) and pain associated with cancer, fibromyalgia and migraine associated pain; for treating tinnitus, functional bowel disorders (non-ulcer dyspepsia, non-cardiac chest pain and irritable bowel syndrome) and neurodegenerative diseases (Alzheimer's disease, ALS, motor neuron disease, Parkinson's disease, muscular sclerosis, macular degeneration and glaucoma), for neuroprotection (treating neurodegeneration following stroke, cardiac arrest, pulmonary bypass, traumatic brain injury and spinal cord injury) and for preventing or reducing dependence/ tolerance/reverse tolerance to a dependence-inducing agent (such as opioids, CNS depressants, psychostimulants and nicotine).

U.S. Pat. No. 6,169,116 describes tetrahydronaphthalenamines as sodium channel blockers in a rat hippocampal veratridine induced glutamate inhibition assay (modification of M. J. Leach et al., *Epilepsia*, 1986, 27, 490–497 and *Stroke*, 1993, 24, 1063–1067 using exogenous glutamate) and in a veratridine binding assay (J. B. Brown, *Journal of Neuroscience*, 1986, 6, 2064–2070), as agents for reducing ischemia-induced neuronal damage and ensuing symptoms in a rat middle cerebral artery (MCA) occlusion model (A. Tamura et al., J. Cereb. Blood Flow Metabol., 1981, 1, 53–60; A. Sauter and M. Rudin, Stroke, 1986, 17, 1228–1234) and methods for the treatment of any clinical condition involving a component of cerebral anoxia, hypoxia or ischemia (ischemic damage to grey and white matter) as a result of stroke, subarachnoid hemorrhage, brain and spinal cord injury/trauma, high intracranial pressure, multi-infarct dementia or vascular dementia, as the result of any surgical procedure potentially associated with cerebral anoxia, hypoxia and/or ischemia (cardiac bypass, operations on extracerebral vessels), as the result of any pathology, disorder or clinical condition involving glutamate release in their etiology (including psychiatric disorders (such as schizophrenia, depression, anxiety, panic attacks, attention deficit and cognitive disorders or social withdrawal), hormonal conditions (such as excess GH (as in diabetes mellitus, angiopathy or acromegaly) or LH (as in prostate hypertrophy, menopausal syndrome] secretion or corticosterone secretion in stress)), metabolic induced brain damage (hypolycemia, non-ketotic hyperglycinaemia (glycine encephalopathy), sulphite oxidase deficiency or hepatic encephalopathy associated with liver failure), emesis, spasticity, tinnitus, pain (as a result of cancer or arthritis) and drug abuse and withdrawal (as a result of the use of ethanol, opiate (including synthetics with opiate-like effects), cocaine, amphetamine, barbiturate and other sedatives and benzodiazepines)), as the result of any pathology involving neuronal damage (including neurodegenerative disorders such as Alzheimer's, Huntington's or Parkinson's diseases, virus induced neurodegeneration (including HIV), ALS, supra-nuclear palsy, olivoponto-cerebellar atrophy (OPCA) and the actions of environmental, exogenous neurotoxins.

U.S. Pat. No. 6,172,085 describes cyclic ether compounds as sodium channel blockers in a rat cerebral cortex fraction binding model and methods for treating central nervous system (CNS) diseases and disorders such as CNS ischemia, CNS trauma (brain trauma, spinal cord injury or whiplash injury), epilepsy, neurodegenerative diseases (ALS, Alzheimer's disease, Huntington's chorea, Parkinson's disease or diabetic neuropathy), vascular dementia (multi-infarct dementia or Binswanger's disease), manic-depressive psychosis, depression, schizophrenia, chronic pain, trigeminal neuralgia, migraine and cerebral edema.

U.S. Pat. No. 6,051,583 describes substituted 2,3,3a,4,9,9a-hexahydro-8-hydroxy-1H-benz[f]indole derivatives as sodium channel blockers in a BTX-binding assay (S. W. Postma & W. A. Catterall, *Mol. Pharmacol.*, 1984 25, 219–227) and in patch-clamp experiments (W. A. Catterall, *Trends Pharmacol. Sci.*, 1987, 8, 57–65), as anticonvulsants in a mouse MES model (M. A. Rogawski and R. J. Porter, Pharmacol. Rev., 1990, 42, 223–286), as neuroprotective agents in a veratridine induced glutamate inhibition assay (S. Villauneva, P. Frenz, Y. Dragnic and F. Orrego, *Brain Res.*, 1988, 461, 377–380) and in a rat-MCAO-model (U. Pschorn and A. J. Carter, *J. Stroke Cerebrovascular Diseases*, 1996, 6, 93–99) and methods for treating neurodegenerative diseases (resulting from arrhythmia, spasm and cardiac and cerebral ischaemia, hypoglycaemia, hypoxia, anoxia, brain trauma, cerebral oedema, stroke and perinatal asphyxia) and those associated with epilepsy, amylotropic lateral sclerosis, Huntington's disease, Alzheimer's disease, Parkinson's disease, cyclophrenia, hypotonia, cardiac infarct, disorders of heart rhythm, angina pectoris, pain (nociceptor pain, neuropathic pain, pain resulting from damage to the peripheral or central nervous system (after amputation, paraplegia, herpes or in diabetic polyneuropathy) and pain caused by functional disorders (migraine and back pain)).

PCT application WO 01/23570 describes voltage-gated sodium channel β1A subunit splice variant nucleic acids and proteins as useful in the treatment of neuropathic pain. PCT application WO 00/61231 describes the use of sodium channel antagonists for treating diseases mediated or exacerbated by sensory neuronal apoptosis: in particular, pain states (such as chronic pain) following nerve insult associated with tissue damage (due to injury or infection), neurodegenerative diseases (such as multiple sclerosis and Parkinson's disease) and inflammation. PCT application WO 00/02865 describes the use of pharmaceutical agents in blocking the activity of voltage-sensitive sodium channels for treating neuronal damage resulting from acute events such as ischemia or hypoxia or from neurodegenerative diseases such as Alzheimer's disease, Parkinson's disease, Huntington's disease, or lateral amyotrophic sclerosis.

SUMMARY OF THE INVENTION

The present invention provides aroyl pyrrole heteroaryl methanone and methanol compounds as agents for treating or modulating a central nervous system disorder selected from Formula (I) or Formula (II):

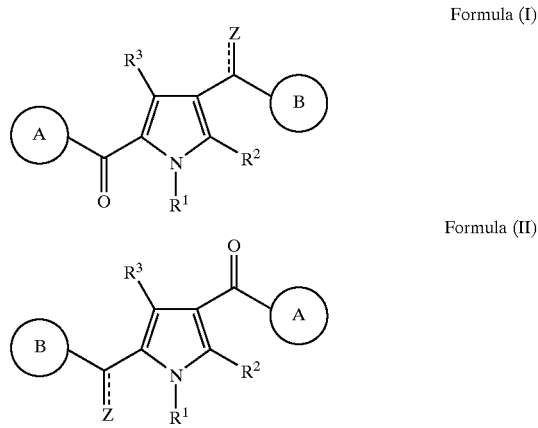

Formula (I)

Formula (II)

wherein
A is selected from the group consisting of
    aryl (optionally substituted with 1 to 4 substituents independently selected from the group consisting of halogen, $C_{1-8}$alkyl, $C_{1-8}$alkoxy, hydroxy, hydroxy($C_{1-8}$)alkyl, hydroxy($C_{1-8}$)alkoxy, (halo)$_{1-3}$($C_{1-8}$)alkyl and (halo)$_{1-3}$($C_{1-8}$)alkoxy) and
    heteroaryl (optionally substituted on 1 to 4 available carbon atom ring members with a substituent selected from the group consisting of halogen, $C_{1-8}$alkyl, $C_{1-8}$alkoxy, hydroxy, hydroxy($C_{1-8}$)alkyl, hydroxy($C_{1-8}$)alkoxy, (halo)$_{1-3}$($C_{1-8}$)alkyl and (halo)$_{1-3}$($C_{1-8}$)alkoxy; and, optionally substituted on available nitrogen atom ring members with a substituent selected from the group consisting of $C_{1-8}$alkyl, hydroxy($C_{1-8}$)alkyl and (halo)$_{1-3}$($C_{1-8}$)alkyl);
B is selected from heteroaryl optionally substituted on 1 to 4 available carbon atom ring members with a substituent selected from the group consisting of halogen, $C_{1-8}$alkyl, $C_{1-8}$alkoxy, hydroxy, hydroxy($C_{1-8}$)alkyl, hydroxy($C_{1-8}$)alkoxy, (halo)$_{1-3}$($C_{1-8}$)alkyl and (halo)$_{1-3}$($C_{1-8}$)alkoxy; and, optionally substituted on available nitrogen atom ring members with a substituent selected from the group consisting of $C_{1-8}$alkyl, $C_{2-8}$alkenyl, hydroxy($C_{1-8}$)alkyl, (halo)$_{1-3}$($C_{1-8}$)alkyl and oxido;
Z is selected from the group consisting of oxo and hydroxy;
$R^1$ is selected from the group consisting of:
    $C_{1-8}$-alkyl {wherein alkyl is optionally substituted on a terminal carbon with one substituent selected from the group consisting of $C_{1-8}$alkoxy, —C(O)— (substituted with one substituent selected from the group consisting of H, OH, $C_{1-8}$-alkyl, $C_{1-8}$alkoxy, $NH_2$, —NH($C_{1-8}$)alkyl, —N(($C_{1-8}$)alkyl)$_2$), —NHC(O)— (substituted with one substituent selected from the group consisting of H, OH, $C_{1-8}$alkyl, $C_{1-8}$alkoxy, $NH_2$, —$NH(C_{1-8})$alkyl, —$N((C_{1-8})alkyl)_2)$, —$OC(O)$— (substituted with one substituent selected from the group consisting of H, OH, $C_{1-8}$alkyl, $C_{1-8}$alkoxy, $NH_2$, —$NH(C_{1-8})$alkyl, —$N((C_{1-8})alkyl)_2)$, $NH_2$, —$NH(C_{1-8})$alkyl, —$N((C_{1-8})$alkyl$)_2$, —$S(C_{1-8})$alkyl, —$SO_2(C_{1-8})$alkyl, cyano, (halo)$_{1-3}$, hydroxy and nitro}, cycloalkyl and aryl {wherein cycloalkyl and aryl are optionally substituted with 1 to 4 substituents independently selected from the group consisting of cyano, halo, hydroxy and nitro; and, wherein cycloalkyl and aryl are optionally substituted with one substituent selected from the group consisting of $C_{1-8}$alkyl, (wherein alkyl is optionally substituted on a terminal carbon with one substituent selected from the group consisting of $NH_2$, —$NH(C_{1-8})$alkyl, —$N((C_{1-8})alkyl)_2$, cyano, (halo)$_{1-3}$, hydroxy and nitro), $C_{1-8}$alkoxy, $NH_2$, —$NH(C_{1-8})$alkyl and —$N((C_{1-8})$alkyl$)_2$};

$R^2$ and $R^3$ are independently selected from the group consisting of hydrogen, $C_{1-8}$alkyl and halogen;

and pharmaceutically acceptable acid addition salts, quaternary ammonium salts and N-oxides thereof.

Embodiments of the present invention include a pharmaceutical composition comprising a pharmaceutically acceptable carrier and a compound selected from Formula (I) or Formula (II) and a method for use of a compound selected from Formula (I) or Formula (II) for treating or modulating a central nervous system disorder.

DETAILED DESCRIPTION OF THE INVENTION

Embodiments of the present invention include compounds selected from Formula (I) or Formula (II) wherein A is selected from aryl optionally substituted with 1 to 4 substituents independently selected from the group consisting of halogen, $C_{1-4}$alkyl, $C_{1-4}$alkoxy, hydroxy, hydroxy($C_{1-4}$)alkyl, hydroxy($C_{1-4}$)alkoxy, (halo)$_{1-3}(C_{1-4})$alkyl and (halo)$_{1-3}(C_{1-4})$alkoxy; wherein aryl is selected from an aromatic monocyclic ring having six members or an aromatic bicyclic ring having ten members.

Preferably, A is selected from the group consisting of phenyl and naphthalenyl optionally substituted with 1 to 4 substituents, as previously described.

More preferably, A is selected from phenyl optionally substituted with 1 to 4 substituents, as previously described.

Preferably, the aryl substituents of A are independently selected from the group consisting of halogen, $C_{1-4}$alkyl and hydroxy.

More preferably, the aryl substituents of A are independently selected from the group consisting of chlorine, fluorine, methyl and hydroxy.

Most preferably, the aryl substituents of A are independently selected from the group consisting of chlorine, fluorine and methyl.

Embodiments of the present invention include compounds selected from Formula (I) or Formula (II) wherein A is selected from heteroaryl optionally substituted on 1 to 4 available carbon atom ring members with a substituent selected from the group consisting of halogen, $C_{1-4}$alkyl, $C_{1-4}$alkoxy, hydroxy, hydroxy($C_{1-4}$)alkyl, hydroxy($C_{1-4}$)alkoxy, (halo)$_{1-3}(C_{1-4})$alkyl and (halo)$_{1-3}(C_{1-4})$alkoxy; and, optionally substituted on available nitrogen atom ring members with a substituent selected from the group consisting of $C_{1-4}$alkyl, hydroxy($C_{1-4}$)alkyl and (halo)$_{1-3}(C_{1-4})$alkyl; wherein heteroaryl is selected from an aromatic monocyclic ring having five members of which at least one member is a N, O or S atom and which optionally contains one, two or three additional N atoms, an aromatic monocyclic ring having six members of which one, two or three members are a N atom, an aromatic bicyclic ring having nine members of which at least one member is a N, O or S atom and which optionally contains one, two or three additional N atoms or an aromatic bicyclic ring having ten members of which one, two or three members are a N atom.

Preferably, the heteroaryl of A is selected from the group consisting of furyl, thienyl, pyrrolyl, oxazolyl, thiazolyl, imidazolyl, pyrazolyl, isoxazolyl, isothiazolyl, triazolyl, pyridinyl, pyridazinyl, pyrimidinyl, pyrazinyl, quinolinyl and isoquinolinyl optionally substituted on 1 to 4 available carbon atom ring members with a substituent, as previously described; and, optionally substituted on available nitrogen atom ring members with a substituent, as previously described.

More preferably, the heteroaryl of A is selected from the group consisting of thienyl, pyridinyl, quinolinyl and isoquinolinyl optionally substituted on 1 to 4 available carbon atom ring members with a substituent, as previously described; and, optionally substituted on available nitrogen atom ring members with a substituent, as previously described.

Most preferably, the heteroaryl of A is selected from the group consisting of thienyl and pyridinyl optionally substituted on 1 to 4 available carbon atom ring members with a substituent, as previously described; and, optionally substituted on available nitrogen atom ring members with a substituent, as previously described.

Preferably, the heteroaryl substituents of A optionally substituted on 1 to 4 available carbon atom ring members are independently selected from the group consisting of halogen and $C_{1-4}$alkyl; and, optionally substituted on available nitrogen atom ring members are selected from $C_{1-4}$alkyl.

More preferably, the heteroaryl substituents of A optionally substituted on 1 to 4 available carbon atom ring members are independently selected from the group consisting of chlorine, fluorine and methyl; and, optionally substituted on available nitrogen atom ring members are selected from methyl.

Embodiments of the present invention include compounds selected from Formula (I) or Formula (II) wherein B is heteroaryl optionally substituted on 1 to 4 available carbon atom ring members with a substituent selected from the group consisting of halogen, $C_{1-4}$alkyl, $C_{1-4}$alkoxy, hydroxy, hydroxy($C_{1-4}$)alkyl, hydroxy($C_{1-4}$)alkoxy, (halo)$_{1-3}$ ($C_{1-4}$)alkyl and (halo)$_{1-3}(C_{1-4})$alkoxy; and, optionally substituted on available nitrogen atom ring members with a substituent selected from the group consisting of $C_{1-4}$alkyl, $C_{2-4}$alkenyl, hydroxy($C_{1-4}$)alkyl, (halo)$_{1-3}(C_{1-4})$alkyl and oxido; wherein heteroaryl is selected from an aromatic monocyclic ring having five members of which at least one member is a N, O or S atom and which optionally contains one, two or three additional N atoms, an aromatic monocyclic ring having six members of which one, two or three members are a N atom, an aromatic bicyclic ring having nine members of which at least one member is a N, O or S atom and which optionally contains one, two or three additional N atoms or an aromatic bicyclic ring having ten members of which one, two or three members are a N atom.

Preferably, the heteroaryl of B is selected from the group consisting of furyl, thienyl, pyrrolyl, oxazolyl, thiazolyl, imidazolyl, pyrazolyl, isoxazolyl, isothiazolyl, triazolyl, pyridinyl, pyridazinyl, pyrimidinyl, pyrazinyl, quinolinyl, isoquinolinyl and quinoxalinyl optionally substituted on 1 to 4 available carbon atom ring members with a substituent, as previously described; and, optionally substituted on available nitrogen atom ring members with a substituent, as previously described.

More preferably, the heteroaryl of B is selected from the group consisting of furyl, thienyl, pyrrolyl, imidazolyl, pyridinyl, quinolinyl and isoquinolinyl optionally substituted on 1 to 4 available carbon atom ring members with a substituent, as previously described; and, optionally substituted on available nitrogen atom ring members with a substituent, as previously described.

Most preferably, the heteroaryl of B is selected from the group consisting of thienyl, imidazolyl and pyridinyl optionally substituted on 1 to 4 available carbon atom ring members with a substituent, as previously described; and, optionally substituted on available nitrogen atom ring members with a substituent, as previously described.

Preferably, the substituents of B optionally substituted on 1 to 4 available carbon atom ring members are independently selected from the group consisting of halogen and $C_{1-4}$alkyl; and, optionally substituted on a nitrogen atom ring member are selected from oxido.

More preferably, the substituents of B optionally substituted on 1 to 4 available carbon atom ring members are independently selected from the group consisting of chlorine and methyl; and, optionally substituted on a nitrogen atom ring member are selected from oxido.

Embodiments of the present invention include those compounds
wherein, $R^1$ is selected from the group consisting of:
$C_{1-4}$alkyl {wherein alkyl is optionally substituted on a terminal carbon with one substituent selected from the group consisting of $C_{1-4}$alkoxy, —C(O)— (substituted with one substituent selected from the group consisting of H, OH, $C_{1-4}$alkyl, $C_{1-4}$alkoxy, $NH_2$, —NH($C_{1-4}$)alkyl, —N(($C_{1-4}$)alkyl)$_2$), —NHC(O)— (substituted with one substituent selected from the group consisting of H, OH, $C_{1-4}$alkyl, $C_{1-4}$alkoxy, $NH_2$, —NH($C_{1-4}$)alkyl, —N(($C_{1-4}$)alkyl)$_2$), —OC(O)— (substituted with one substituent selected from the group consisting of H, OH, $C_{1-4}$alkyl, $C_{1-4}$alkoxy, $NH_2$, —NH($C_{1-4}$)alkyl, —N(($C_{1-4}$)alkyl)$_2$), $NH_2$, —NH($C_{1-4}$)alkyl, —N(($C_{1-4}$)alkyl)$_2$, —S($C_{1-4}$)alkyl, —SO$_2$($C_{1-4}$)alkyl, cyano, (halo)$_{1-3}$, hydroxy and nitro},
cycloalkyl and aryl {wherein cycloalkyl and aryl are optionally substituted with 1 to 4 substituents independently selected from the group consisting of cyano, halo, hydroxy and nitro; and, wherein cycloalkyl and aryl are optionally substituted with one substituent selected from the group consisting of $C_{1-4}$alkyl, (wherein alkyl is optionally substituted on a terminal carbon with one substituent selected from the group consisting of $NH_2$, —NH($C_{1-4}$)alkyl, —N(($C_{1-4}$)alkyl)$_2$, cyano, (halo)$_{1-3}$, hydroxy and nitro), $C_{1-4}$alkoxy, $NH_2$, —NH($C_{1-4}$)alkyl and —N(($C_{1-4}$)alkyl)$_2$}.

Preferably, $R^1$ is selected from $C_{1-4}$alkyl optionally substituted on a terminal carbon with a substituent, as previously described.

More preferably, $R^1$ is selected from $C_{1-4}$alkyl.

Preferably, the optional substituent on the terminal carbon of $C_{1-4}$alkyl is selected from the group consisting of $C_{1-4}$alkoxy, $NH_2$, —NH($C_{1-4}$)alkyl, —N(($C_{1-4}$)alkyl)$_2$, cyano, (halo)$_{1-3}$, hydroxy and nitro.

Embodiments of the present invention include those compounds wherein, preferably, $R^2$ and $R^3$ are independently selected from the group consisting of hydrogen, $C_{1-4}$alkyl and halogen. More preferably, $R^2$ and $R^3$ are independently selected from the group consisting of hydrogen and $C_{1-4}$alkyl. Most preferably, $R^2$ and $R^3$ are independently selected from the group consisting of hydrogen and methyl.

Exemplifying the invention is a compound selected from Formula (I):

TABLE 1

Formula (I)

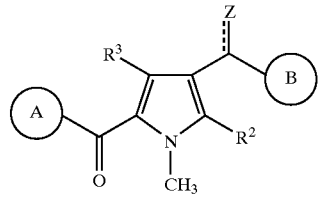

wherein A, B, Z, $R^2$ and $R^3$ are dependently selected from

| Cpd | A | B | Z | $R^2$ | $R^3$ |
|---|---|---|---|---|---|
| 1 | 4-Cl—Ph | 4-pyridinyl | O | H | H; |
| 2 | Ph | 4-pyridinyl | O | H | H; |
| 3 | 4-Me—Ph | 4-pyridinyl | O | H | H; |
| 5 | 4-Cl—Ph | 4-pyridinyl | O | H | H; |
| 6 | 4-Cl—Ph | 2-pyridinyl | O | H | H; |
| 12 | 4-Cl—Ph | 4-pyridinyl | OH | H | H; |
| 13 | 4-Cl—Ph | 1H-imidazol-5-yl | O | H | H; |
| 14 | 4-Cl—Ph | 1-Me-4-pyridinyl | O | H | H; |
| 15 | 4-Cl—Ph | 1-oxido-4-pyridinyl | O | H | H; |
| 16 | 4-Cl—Ph | 1-oxido-4-pyridinyl | OH | H | H; |
| 18 | 4-Cl—Ph | 4-pyridinyl | OH | $CH_3$ | $CH_3$; |
| and, | | | | | |
| 19 | 4-Cl—Ph | 2-Cl-4-pyridinyl | O | H | H; | and pharmaceutically acceptable acid addition salts, quaternary ammonium salts and N-oxides thereof.

Exemplifying the invention is a compound selected from Formula (II):

TABLE 2

Formula (II)

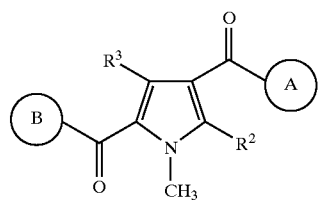

wherein B, A, $R^2$ and $R^3$ are dependently selected from

| Cpd | B | A | $R^2$ | $R^3$ |
|---|---|---|---|---|
| 4 | 2-thienyl | 4-pyridinyl | H | H; |
| 7 | 3-pyridinyl | 4-F—Ph | H | H; |
| 8 | 3-pyridinyl | 2-naphthalenyl | H | H; |
| 9 | 6-Cl-3-pyridinyl | 4-Cl—Ph | H | H; |
| 10 | 2-pyridinyl | 4-F—Ph | H | H; |
| 11 | 4-pyridinyl | 4-F—Ph | H | H; |
| and, | | | | |
| 17 | 3-pyridinyl | 4-F—Ph | $CH_3$ | $CH_3$; | and pharmaceutically acceptable acid addition salts, quaternary ammonium salts and N-oxides thereof.

An embodiment of the present invention includes a pharmaceutical composition comprising a pharmaceutically acceptable carrier and a compound selected from Formula (I) or Formula (II).

To prepare the pharmaceutical compositions of this invention, one or more compounds selected from Formula (I) or Formula (II) are intimately admixed with a pharmaceutical carrier according to conventional pharmaceutical compounding techniques, which carrier may take a wide variety of forms depending on the form of preparation desired for administration (e.g., oral, topical, suppository or parenteral).

In preparing the compositions in oral dosage form, any of the usual pharmaceutical media may be employed. Thus, for liquid oral preparations, such as suspensions, elixirs and solutions suitable carriers and additives include water, glycols, oils, alcohols, flavoring agents, preservatives, coloring agents and the like. For solid oral preparations such as powders, capsules and tablets or for topical preparations such as creams suitable carriers and additives include starches, sugars, diluents, granulating agents, lubricants, binders, disintegrating agents and the like.

Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. For topical agents, suitable diluents, granulating agents, lubricants and disintegrating agents should be employed to aid dispersion and absorbtion.

The pharmaceutical compositions herein may contain, per dosage unit (e.g., tablet, capsule, powder, injection, teaspoonful, suppository and the like) from about 0.001 mg to about 500 mg of the active ingredient.

The terms used in describing the invention are commonly used and known to those skilled in the art. As used herein, the following abbreviations have the indicated meanings:

| | |
|---|---|
| DCE | 1,2-dichloroethane |
| Et$_2$O | Diethyl ether |
| EtOH | Ethanol |
| h | Hour |
| K$_2$CO$_3$ | Potassium carbonate |
| MeOH | Methanol |
| mm | Minute |
| MTBE | Methyl-t-butyl ether |
| 2-PrOH | 2-Propanol |

General Synthetic Methods

Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art.

SCHEME A exemplifies the preparation of target compounds wherein A is at the 2-position of the pyrrole and B is at the 4-position and Z is oxo. Alternatively, by varying the starting materials and using the same conditions outlined in Scheme A, target compounds wherein B is at the 2-position of the pyrrole and A is at the 4-position and Z is oxo may be prepared.

Referring to Scheme A, in the first step a simple pyrrole Compound A1 is acylated with an appropriately substituted aroyl chloride Compound A2 (A—C(O)Cl) to produce an aroyl pyrrole Compound A3. This acylation may be carried out by simply heating the aroyl chloride Compound A2 and the pyrrole Compound A1 in an aprotic solvent. The temperature of the acylation will vary depending upon the desired rate of reaction and the substituents of pyrrole Compound A1. Preferably, the acylation is carried out at a temperature of from about 50° C. to about 250° C.

Subsequently, the aroyl pyrrole Compound A3 is acylated at the 4-position in a Friedel-Crafts reaction with a heteroaryl methanone chloride compound (B—C(Z)Cl; where Z is oxo) Compound A4 to produce the desired product Compound A5. The Friedel-Crafts reaction is preferably carried out at a temperature of from about 0° C. to about 100° C. Suitable Friedel-Crafts Lewis acid catalysts include aluminum chloride, zinc chloride, BF$_3$ or TiCl$_4$. Suitable solvents include methylene chloride, 1,2-dichloroethane, carbon tetrachloride, nitromethane, nitrobenzenene, dichlorobenzene or chloroform.

SCHEME A

An alternative route to the preparation of compounds wherein A is an aryl or heteroaryl group at the 2-position of the pyrrole and B is a heteroaryl group at the 4-position and Z is oxo is illustrated in SCHEME B.

The 2-aroylpyrrole Compound A3 (wherein A is an aryl group and Z is oxo) is subjected to Freidel-Crafts formylation using 1,1-dichloromethyl methyl ether and a suitable Friedel-Crafts Lewis acid catalyst such as aluminum chloride, zinc chloride, BF$_3$ or TiCl$_4$ to give the 2-aroyl-4-pyrrol-2 carboxaldehyde Compound-B1. The Friedel-Crafts reaction is carried out at a temperature of from about −40° C. to about 50° C. Suitable solvents include methylene chloride, 1,2-dichloroethane, carbon tetrachloride nitromethane, nitrobenzene, dichlorobenzene, chloroform or mixtures thereof. The aldehyde was then caused to react with the B-metal Compound B2 (wherein B is a heteroaryl group) to give the carbinol Compound B3. Suitable heteroaryl-metal compounds include organolithium, organomagnesium (Grignard) and organozinc compounds. Such heteroaryl-metal compounds may be prepared by metal halogen exchange between a halo heteroaromatic compound and a simple organometallic such as n-butyllithium, ethyl magnesium bromide or diethyl zinc. Preferred solvents for this for this two step procedure are ethereal solvents such as diethyl ether or THF. The metal halogen-halogen exchange reaction may be carried out at temperatures of from about −78° C. to about 25° C. Addition of the heteroaryl-metal compound to the aldehyde can be carried out at temperature of from about −78° C. to about 50° C.

The carbinol Compound B3 was then oxidized to the corresponding ketone Compound B4 using a suitable oxidant (O) such as manganese dioxide, chromium trioxide or potassium permanganate. The manganese dioxide oxidation was carried out by stirring in a halocarbon or hydrocarbon solvent. When the desired heterocyclic starting material bears an acidic or sensitive functionality, the overall sequence may be carried out with a protecting group such as trityl or benzyl on the heterocycle. The protecting group may then be removed after the organometallic addition by hydrogenolysis or acid treatment.

SCHEME B

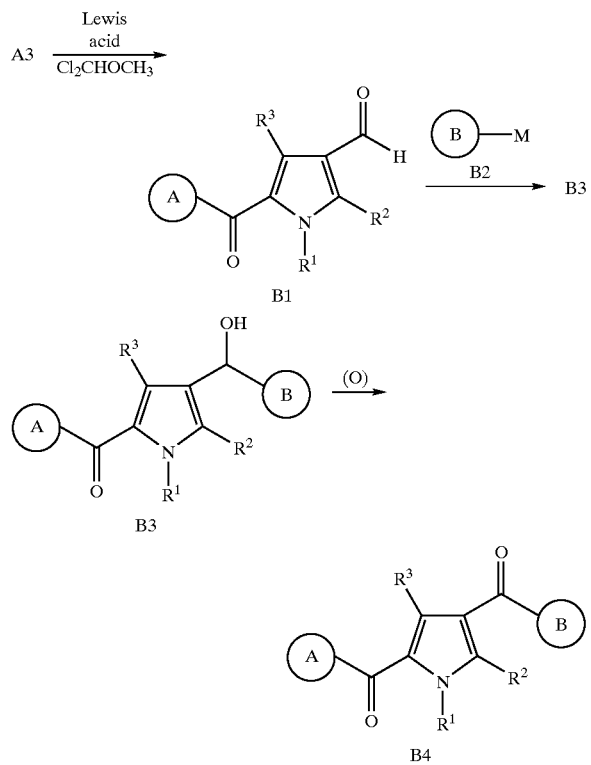

SCHEME C illustrates the formation of simple derivatives of the instant compounds wherein A is an aryl group at the 2-position of the pyrrole and B is a heteroaryl group at the 4-position and Z is oxo.

When the 2-aroyl-4-heteroaroylpyrrole Compound C1 is treated with an alkyl or alkenyl halide, the corresponding alkyl or alkenyl quaternary ammonium salt Compound C2 (wherein X is alkyl or alkenyl) is produced. The reaction may be carried out in an inert solvent such as ethyl acetate, benzene, toluene, THF or ether. It may be carried out at from about 25° C. to the reflux temperature of the solvent.

When the 2-aroyl-4-heteroaroylpyrrole Compound C1 is treated with a peracid such as m-chloroperbenzoic acid or peracetic acid, the corresponding oxido Compound C2 (wherein X is O) is produced. The reaction may be carried out in an inert solvent such as methylene chloride or chloroform at temperatures of about 0° C. to about 50° C.

SCHEME C

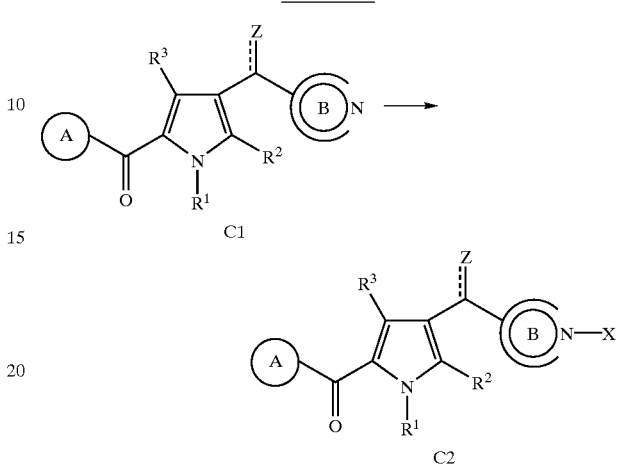

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201–217; J. Pharm. Sci., 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Specific Synthetic Methods

Specific compounds which are representative of this invention may be prepared as per the following examples offered by way of illustration and not by way of limitation. Also, examples specifically used to prepare intermediates for the further synthesis of compounds of the invention are designated by "Procedure." No attempt has been made to optimize the yields obtained in any of the reactions. One skilled in the art would know how to increase such yields through routine variations in reaction times, temperatures, solvents and/or reagents.

Example 1

[5-(4-Chlorobenzoyl)-1-methyl-1H-pyrrol-3-yl] pyridin-4-ylmethanone (Cpd 1)

A solution of 17.5 g (0.08 mole) of (4-chlorophenyl)(1-methyl-1H-pyrrol-2-yl)methanone, 14.4 g (0.088 mole) of isonicotinoyl chloride and 26.6 g of aluminum chloride (0.2 mole) in 280 mL of DCE was heated under reflux for 16 h. After cooling, the mixture was partitioned between $CH_2Cl_2$ and dilute NaOH solution. The organic layer was dried and the solvent was evaporated in vacuo. The residue was triturated with ether. The resulting solid was recrystallized from 2-PrOH to give 7 g (27%) of the title compound, mp 174–175° C. ES-MS m/z=325 ($M^+$+H). $^1$H NMR (300 MHz, $CDCl_3$) δ 4.1 (s, 3H); 7.1 (s, 1H); 7.3(dd, 2H); 7.42 (dd, 2H); 7.45 (s, 1H); 7.8 (dd, 2H); 8.8 (dd, 2H). Anal calc'd for: $C_{18}H_{13}ClN_2O_2$: C, 66.57; H, 4.03; N, 8.63. Found: C, 66.34; H, 3.94; N, 8.53.

Example 2

(5-Benzoyl-1-methyl-1H-pyrrol-3-yl)pyridin-4-ylmethanone (Cpd 2)

Following the protocol of Example 1 and employing (1-methyl-1H-pyrrol-2-yl)-phenylmethanone in place of (4-chlorophenyl)(1-methyl-1H-pyrrrol-2-yl)methanone, the title compound was obtained in crude form and purified by flash chromatography (20% acetone in hexane): mp 127–129 ° C. ES-MS m/z=290 ($M^+$+H). $^1$H NMR (300 MHz, DMSO-$d_6$) δ 4.05 (s, 3H); 7.0 (s, 1H); 7.6 (m, 5H); 7.8 (m, 4H); 7.95 (s, 1H).

Example 3

[1-Methyl-5-(4-methylbenzoyl)-1H-pyrrol-3-yl] pyridin-4-ylmethanone Hydrochloride (Cpd 3)

Following the protocol of Example 1 and employing (1-methyl-1H-pyrrol-2-yl)-p-tolylmethanone in place of (4-chlorophenyl)(1-methyl-1H-pyrrrol-2-yl)methanone, the title compound was obtained in crude form, was treated with 3N HCl to give the hydrochloride salt and recrystallized from MeOH/EtOH: mp 134–136° C. ES-MS m/z=305 ($M^+$+H). $^1$H NMR (300 MHz, DMSO-$d_6$) δ 2.44 (s, 3H); 4.0 (s, 3H); 7.03 (s, 1H); 7.4 (dd, 2H); 7.75 (dd, 2H); 8.0 (dd, 2H); 8.05 (s, 1H); 8.95 (dd, 2H). Anal calc'd for: $C_{19}H_{16}N_2O_2$·HCl: C, 66.96; H, 5.03; N, 8.22. Found: C, 67.2; H, 4.99; N, 8.0.

Example 4

[1-Methyl-5-(thiophene-2-carbonyl)-1H-pyrrol-3-yl] pyridin-4-ylmethanone hydrochloride (Cpd 4)

Following the protocol of Example 1 and employing (1-methyl-1H-pyrrol-2-yl)-thiophen-2-ylmethanone place of (4-chlorophenyl)(1-methyl-1H-pyrrrol-2-yl)methanone, the title compound was obtained in crude form, treated with 3N HCl to give the hydrochloride salt and purified by flash chromatography (10% MeOH in $CH_2Cl_2$): mp 243–245° C. ES-MS m/z=297 ($M^+$+H). $^1$H NMR (300 MHz, DMSO-$d_6$) δ 4.0 (s, 3H); 7.3 (t, 1H); 7.4 (s, 1H); 7.9 (m, 3H); 8.02 (s, 1H); 8.1 (d, 1H); 8.95 (dd, 2H). Anal calc'd for: $C_{16}H_{12}N_2O_2S$·HCl: C, 57.74; H, 3.94; N, 8.42. Found: C, 57.61; H, 3.99; N, 8.21.

Example 5

[5-(4-Chlorobenzoyl)-1-methyl-1H-pyrrol-3-yl] pyridin-3-ylmethanone hydrochoride hydrate [2:1:1] (Cpd 5)

Following the protocol of Example 1 and employing nicotinoyl chloride hydrochloride in place of isonicotinoyl chloride hydrochloride, the title compound was obtained in crude form and purified by flash chromatography (30% acetone in hexane). The hydrochloride salt was obtained from THF/$Et_2$O/HCl: mp 138–140° C. ES-MS m/z=325 ($M^+$+H). $^1$H NMR (300 MHz, DMSO-$d_6$) δ 4.05 (s, 3H); 5.0 (br s, 2H), 7.1 (s, 1 H); 7.62 (dd, 2H); 7.72 (m, 1H); 7.82 (dd, 2H); 8.1(s, 1H); 8.35 (m, 3H); 8.9 (m, 1H); 9.07 (s, 1H). Anal calc'd for: $C_{18}H_{13}ClN_2O_2$. 0.5 HCl. 0.5 $H_2O$: C, 66.96; H, 5.03; N, 8.22. Found: C, 67.2; H, 4.99; N, 8.0.

Example 6

[5-(4-Chlorobenzoyl)-1-methyl-1H-pyrrol-3-yl] pyridin-2-yl-methanone (Cpd 6)

Following the protocol of Example 1 and employing picolinoyl chloride hydrochloride in place of isonicotinoyl chloride hydrochloride, the title compound was obtained in 36% yield, recrystallized twice from 2-PrOH and once from EtOAc: mp 138–139° C. ES-MS m/z=325 ($M^+$+H). $^1$H NMR (300 MHz, $CDCl_3$) δ 4.1 (s, 3H); 7.5 (dd, 2H); 7.55

(m, 2H); 7.84 (dd, 2H); 7.9 (t, 1H); 8.1(d, 1H); 8.35 (s, 1H); 8.7 (d, 1H). Anal calc'd for: $C_{18}H_{13}ClN_2O_2$: C, 66.57; H, 4.03; N, 8.63. Found: C, 67.2; H, 4.99; N, 8.0. Found: C, 66.2; H, 4.11; N, 8.55.

Procedure 1

(1-Methyl-1H-pyrrol-2-yl)pyridin-3-yl methanone

A mixture of 25 g (0.14 moles) of nicotinoyl chloride hydrochloride and 10.4 mL (0.14 mole) of N-methylpyrrole was heated under reflux in 200 mL of dry toluene while a nitrogen stream was bubbled slowly through the reaction mixture. After refluxing overnight the reaction mixture was cooled and the solid filtered off. The solid was converted the free base by partitioning between $Et_2O/3N$ NaOH. The organics were washed with water, brine and dried ($K_2CO_3$). The residue was chromatographed on silica (90:10:1 $CH_2Cl_2$:MeOH:$NH_4OH$) to give 8.9 g of (2-pyridinyl)(1-methyl-1H-pyrrol-2-yl)-methanone (34%) as a gum. CI-MS m/z=188 (M$^+$+H). $^1$H NMR (300 MHz, CDCl$_3$) δ 9.0 (ar, 1H); 8.7 (ar, 1H); 8.1 (ar, 1H); 7.4 (ar, 1H); 6.7 (ar, 1H); 6.2 (ar, 1H), 4.0 (s, 3H).

Example 7

(4-Fluorophenyl)-[1-methyl-5-(pyridine-3-carbonyl)-1H-pyrrol-3-yl]methanone Hydrochloride (Cpd 7)

A solution of 3.33 g (0.015 mole) of (1-methyl-1H-pyrrol-2-yl)-pyridin-3-yl-methanone hydrochloride, 1.94 mL (0.0165mole) of 4-fluorobenzoyl chloride and 5 g of aluminum chloride (0.037 mole) in 50 mL of DCE was stirred at 25° C. for 16 h. The mixture was partitioned between $CH_2Cl_2$ and dilute NaOH solution. The organic layer was dried and the solvent was evaporated in vacuo. The residue was flash chromatographed with 35% acetone in hexane to give 2.14 (46% yield) of the free base. The hydrochloride salt of the title compound was obtained from $Et_2O$/HCl: mp 220–223° C. ES-MS m/z=309 (M$^+$+H). $^1$H NMR (300 MHz, DMSO-d$_6$) δ 4.0 (s, 3H); 6.2 (br s, 2H); 7.16 (s, 1H); 7.35 (t, 2H); 7.85 (m, 1H); 7.95 (m, 2H); 8.1 (s, 1H); 8.4 (d, 1H), 8.95 (d, 1H); 9.05 (s, 1H); 10.5 (br s, 1H). Anal calc'd for: $C_{18}H_{13}FN_2O_2$.HCl: C, 62.71; H, 4.09; N, 8.13. Found: C, 63.08; H, 4.23; N, 8.11.

Example 8

[1-Methyl-5-(pyridine-3-carbonyl)-1H-pyrrol-3-yl]naphthalen-2-yl-methanone (Cpd 8)

Following the protocol of Example 7 and employing 2-naphthoyl chloride hydrochloride in place of 4-fluorobenzoyl chloride and heating at 55° C., the title compound was obtained and recrystallized from EtOAc: mp 132–133° C. ES-MS m/z=341 (M$^+$+H). $^1$H NMR (300 MHz, CDCl$_3$) δ 4.1 (s, 3H); 7.25 (s, 1H); 7.45 (m, 1H); 7.56 (m, 3H); 7.9 (m, 4H); 8.15(d, 1H); 8.35 (s, 1H); 8.8 (d, 1H); 9.05 (s, 1H). Anal calc'd for: $C_{22}H_{16}N_2O_2$: C, 77.63; H, 4.74; N, 8.23. Found: C, 77.14; H, 4.55; N, 8.02.

Procedure 2

(6-Chloropyridin-3-yl)-(1-methyl-1H-pyrrol-2-yl)methanone

Following the protocol for Example 1 and employing 5-chloronicotinoyl chloride hydrochloride in place of nicotinoyl chloride hydrochloride the title compound was obtained. ES-MS m/z=221 (M$^+$+H). $^1$H NMR (300 MHz, CDCl$_3$) δ 4.1 (s, 3H); 6.2 (m, 1H); 6.75 (m, 1H); 7.0 (s, 1H); 7.45 (d, 1H); 8.05 (d, 1H); 8.8 (s, 1H).

Example 9

(4-Chlorophenyl)-[5-(6-chloropyridine-3-carbonyl)-1-methyl-1H-pyrrol-3-yl]methanone (Cpd 9)

Following the protocol of Example 8 and employing (6-chloropyridin-3-yl)-(1-methyl-1H-pyrrol-2-yl) methanone hydrochloride in place of (1-methyl-1H-pyrrol-2-yl)-pyridin-3-ylmethanone hydrochloride and 4-chlorobenzoyl chloride in place of 4-fluorobenzoyl chloride, the title compound was obtained and recrystallized from MTBE: mp 150–152° C. ES-MS m/z=360 (M$^+$+H). $^1$H NMR (300 MHz, CDCl$_3$) δ 4.1 (s, 3H); 7.2 (s, 1H); 7.5 (m, 3H); 7.56 (s, 1H); 7.8 (dd, 2H); 8.05 (d, 1H); 8.8 (s, 1H). Anal calc'd for $C_{18}H_{12}C_2N_2O_2$: 60.19; H, 3.37; N, 7.8. Found: C, 59.9; H, 3.34; N, 7.71.

Procedure 3

(1-Methyl-1H-pyrrol-2-yl)-pyridin-3-yl-methanone hydrochloride

Following the protocol for Example 1 and employing picolinoyl chloride hydrochloride in place of nicotinoyl chloride hydrochloride the title compound was obtained in 38% yield. ES-MS m/z=187 (M$^+$+H). $^1$H NMR (300 MHz, CDCl$_3$) δ 4.05 (s, 3H); 6.2 (m, 1H); 6.95 (m, 1H); 7.32 (m, 1H); 7.42 (m, 1H); 7.86 (m, 1H); 7.95 (d, 1H); 8.7 (d,1H).

Example 10

(4-Fluorophenyl)-[1-methyl-5-(pyridine-2-carbonyl)-1H-pyrrol-3-yl]methanone (Cpd 10)

Following the protocol of Example 7 and employing (1-methyl-1H-pyrrol-2-yl)-pyridin-2-yl-methanone hydrochloride in place of (1-methyl-1H-pyrrol-2-yl)-pyridin-3-yl-methanone hydrochloride, the title compound was obtained in 56% yield. It was recrystallized from 2-PrOH: mp 159–161° C. ES-MS m/z=309 (M$^+$+H). $^1$H NMR (300 MHz, CDCl$_3$) δ 4.1 (s, 3H); 7.2 (m, 2H); 7.5 (m, 2H); 7.9 (m, 4H); 8.05 (d, 1H); 8.7 (d, 1H). Anal calc'd for $C_{18}H_{13}FN_2O_2$; C, 70.12; H, 4.25; N, 9.09. Found: C, 70.01; H, 4.15; N, 8.88.

Procedure 4

(1-Methyl-1H-pyrrol-2-yl)-pyridin-4-ylmethanone hydrochloride

Following the protocol for Example 1 and employing isonicotinoyl chloride hydrochloride in place of nicotinoyl chloride hydrochloride the title compound was obtained. ES-MS m/z=187 (M$^+$+H). $^1$H NMR (300 MHz, CDCl$_3$) δ 4.05 (s, 3H); 6.2 (m, 1H); 6.7 (m, 1H); 7.0 (s, 1H); 7.6 (dd, 2H); 8.75 (dd, 2H).

Example 11

(4-Fluorophenyl)-[1-methyl-5-(pyridine-4-carbonyl)-1H-pyrrol-3-yl]methanone (Cpd 11)

Following the protocol of Example 7 and employing (1-methyl-1H-pyrrol-2-yl)-pyridin-4-yl-methanone hydrochloride in place of (1-methyl-1H-pyrrol-2-yl)-pyridin-3-yl-methanone hydrochloride, the title compound was obtained recrystallized from EtOAc: mp 155–7° C. ES-MS m/z=309 (M$^+$+H). $^1$H NMR (300 MHz, CDCl$_3$) δ 4.1 (s, 3H); 7.2 (m, 3H); 7.5 (s, 1H); 7.6 (dd, 2H); 7.8 (dd, 2H); 8.8 (dd, 2H).

Procedure 5

5-(4-Chlorobenzoyl)-1-methyl-1H-pyrrole-3-carboxaldehyde

To a mixture of 5.05 g (23 mmol) of (4-chlorophenyl)(1-methyl-1H-pyrrrol-2-yl)methanone and 6.11 g (46 mmol) of $AlCl_3$ in 42 mL of 1,2-dichloroethane and 42 mL of nitromethane at −20° C. under argon was added 2.27 mL (25.3 mmol) of 1,1-dichlorodimethyl ether. The mixture was stirred at −20° C. for one hour and at 25° C. for 16 h. It was poured into ice/HCl and extracted with $CH_2Cl_2$. The organic phase was dried ($MgSO_4$) and concentrated. The residue was recrystallized from EtOAc to give 2.5 g (43%) of the title compound as a maroon solid: CI-MS m/z=248 ($M^+$+H). $^1H$ NMR (300 MHz, $CDCl_3$) δ 4.1 (s, 3H); 7.1 (s, 1H); 7.45 (dd, 2H); 7.5 (s, 1H); 7.8 (dd, 2H); 9.8 (s, 1H).

Example 12

(4-Chlorophenyl)-[4-(hydroxypyridin-4-yl-methyl)-1-methyl-1H-pyrrol-2-yl]-methanone (Cpd 12)

A solution of 1.36 g (8.64 mmol) of 4-bromopyridine in 12 mL of ether was cooled to −40° C. under argon and 5.4 mL (8.64 mmol) of 1.6 M n-butyllithium in hexane was added dropwise. A solution of 1.07 g (4.3 mmol) of 5-(4-chloro-benzoyl)-1-methyl-1H-pyrrole-3-carboxaldehyde (obtained from Procedure 5) in 15 mL of THF was added dropwise (exotherm). The reaction was stirred for 5 min and poured into water and extracted with $CH_2Cl_2$. The organic phase was dried ($MgSO_4$) and concentrated. The residue was flash chromatographed (50%acetone/hexane). The trailing spot was concentrated and recrystallized from EtOAc to give 0.74 g (52% yield) of the title compound as a white solid: mp 145–146° C. ES-MS m/z=327 ($M^+$+H). $^1H$ NMR (300 MHz, $CDCl_3$) δ 2.55 (s, 1H); 4.0 (s, 3H); 5.8 (s, 1H); 6.56 (s, 1H); 6.8 (s, 1H); 7.3 (dd, 2H); 7.4 (dd, 2H); 7.75 (dd, 2H); 8.55 (dd, 2H). Anal calc'd for $C_{18}H_{15}ClN_2O_2$: 66.16; H, 4.63; N, 8.57. Found: C, 65.8; H, 4.65; N, 8.63.

Procedure 6

(4-Chlorophenyl )-{4-[hydroxy-(1-trityl-1H-imidazol-4-yl )-methyl]-1-methyl-1H-pyrrol-2-yl}methanone To 4.4 g (0.01 mole) 4-iodo-1-tritylimidazole in 80 mL of $CH_2Cl_2$ was added dropwise 3.3 mL of 3.0 M ethylmagnesium bromide in $Et_2O$. After stirring for 1 h, a solution of 1.0 g (0.004 mole) of 5-(4-chlorobenzoyl)-1-methyl-1H-pyrrole-3-carboxaldehyde in 10 mL of $CH_2Cl_2$ was added dropwise. The resulting reaction mixture was stirred for 2.5 h after which it was poured into water. The solid was filtered off through celite. The organics from the filtrate were separated off, washed with water, brine and dried ($Na_2SO_4$). The solvent was evaporated in vacuo to give 3.1 g of (4-chlorophenyl)-{4-[hydroxy-(1-trityl-1H-imidazol-4-yl)-methyl]-1-methyl-1H-pyrrol-2yl}-methanone: CI-MS m/z=559 ($M^+$+H). $^1HNMR$ ($CDCl_3$) δ 7.7 (m, 5H) 7.4–7.0 (m, 16H); 6.5 (m, 1H); 3.75 (s, 3H).

Procedure 7

(4-Chlorophenyl)-[1-methyl-4-(1-trityl-1H-imidazole-4-carbonyl)-1H-pyrrol-2-yl]methanone A solution 2.2 g of (4-chloro-phenyl)-{4-[hydroxy-(1-trityl-1H-imidazol-4-yl)-methyl]-1-methyl-1H-pyrrol-2-yl}methanone in 50 mL of $CH_2Cl_2$ was stirred with 2.5 g of activated manganese dioxide overnight. The reaction was filtered and the filtrate was evaporated in vacuo to give 2.0 g of (4-chlorophenyl)-[1-methyl-4-(1-trityl-1H-imidazole-4-carbonyl)-1H-pyrrol-2yl]methanone. CI-MS m/z=556 ($M^+$+H).

Example 13

(4-Chlorophenyl)-[4-(3H-imidazole-4-carbonyl)-1-methyl-1H-pyrrol-2-yl]methanone (Cpd 13)

A 2.0 g sample of 1-[5-(4-chlorobenzoyl)-1-methyl-1H-pyrrol-3-yl]-2-(1-trityl-1H-imidazol-4yl)ethanone was stirred in 50 mL of MeOH and 35 mL of 2 N HCl for 5 h. The solvent was evaporated in vacuo and the resulting residue was passed through a Biotage Flash 40L (silica gel; $CH_2Cl_2$:MeOH) to give 0.14 g of (4-chlorophenyl)-[4-(3H-imidazole-4-carbonyl)-1-methyl-1H-pyrrol-2-yl]methanone: mp.198–200° C. CI-MS m/z=314 ($M^+$+H). $^1HNMR$ ($CD_3CN$) δ 8.4 (ar, 1H); 7.9–7.8 (ar, 4H); 7.7 (ar, 1H); 7.6 (ar, 3H); 7.5 (ar, 1H); 4.0 (s, 3H); 2.0 (m, 2H).

Example 14

4-[[5-(4-Chlorobenzoyl )-1-methyl-1H-pyrrol-3-yl] carbonyl]-1-methylpyridinium trifluoromethanesulfonate hydrate [5:1] (Cpd 14)

A mixture of 0.64 g (2 mmol) of [5-(4-chlorobenzoyl)-1-methyl-1H-pyrrol-3-yl]pyridin-4-ylmethanone and 0.22 mL (2 mmol) methyl triflate was stirred for 16 h in 20 mL of $CH_2Cl_2$. The solvent was evaporated and the residue recrystallized from EtOAc to give 0.76 g (77% yield) of the title compound as a white solid: mp 113–114° C. ES-MS m/z=339 ($M^+$+H). $^1H$ NMR (300 MHz, $CDCl_3$) δ 4.0 (s, 3H); 4.55 (s, 3H), 7.32 (dd, 2H); 7.8 (m, 3H); 8.2 (dd, 2H); 9.0 (dd, 2H). Anal calc'd for: $C_{19}H_{16}ClN_2O_2 \cdot CF_3O_3S \cdot 0.2 H_2O$: C, 48.77; H, 3.35; N, 5.68; KF,0.73. Found: C, 48.91; H, 3.5; N, 5.57; KF,1.03.

Example 15

(4-Chlorophenyl)-[1-methyl-4-(1-oxypyridine-4-carbonyl)-1H-pyrrol-2-yl]methanone (Cpd 15)

A solution of 324 mg (10 mmol) of [5-(4-chlorobenzoyl)-1-methyl-1H-pyrrol-3-yl]pyridin-4-ylmethanone and 300 mg (>10 mmol) m-chloroperbenzoic acid in 5mL $CHCl_3$ for 3 h. The solution was washed with dilute NaOH, dried ($Na_2SO_4$) and concentrated. The residue was recrystallized from EtOAc to give 260 mg (76% yield) of the title compound as a white solid: mp 207–208° C. ES-MS m/z=341 ($M^+$+H). $^1H$ NMR (300 MHz, $CDCl_3$) δ 4.1 (s, 3H); 7.1 (s, 1H); 7.5 (dd, 2H); 7.53 (s, 1H); 7.7 (dd, 2H); 7.8 (dd, 2H); 8.23 (dd, 2H).

Example 16

(4-Chlorophenyl)-{4-[hydroxy-(1-oxy-pyridin-4-yl )methyl]-1-methyl-1H-pyrrol-2-yl}methanone (Cpd 16)

Following the protocol of Example 15 and employing (4-chlorophenyl)-[4-(hydroxypyridin-4-yl-methyl)-1-methyl-1H-pyrrol-2-yl]methanone in place of [5-(4-chlorobenzoyl)-1-methyl-1H-pyrrol-3-yl]pyridin-4-ylmethanone, the title compound was obtained, recrystallized from $CHCl_3$ to give the title compound in 50% yield. ES-MS m/z=344 ($M^+$+H). $^1H$ NMR (300 MHz, DMSO-$d_6$) δ 3.95 (s, 3H); 5.58 (d, 1H); 5.9 (d, 1H); 6.6 (s, 1H); 7.15 (s, 1H); 7.4 (dd, 2H); 7.56 (dd, 2H); 7.7 (dd, 2H); 8.1 (dd, 2H).

Procedure 8

Pyridin-3-yl-(1,3,5-trimethyl-1H-pyrrol-2-yl)methanone

Following the protocol for Example 1 and employing 1,2,4-trimethylpyrrole in place of N-methylpyrrole, the title compound was obtained: mp 195–197° C. CI-MS m/z=215 (M$^+$+H). $^1$HNMR (CDCl$_3$) δ 8.95–8.85 (ar, 2H); 8.7 (ar, 1H); 8.1 (ar, 1H); 5.9 (ar, 1H); 3.8 (s, 3H); 2.3 (s, 3H); 1.7 (s, 3H).

Example 17

(4-Fluorophenyl)-[1,2,4-trimethyl-5-(pyridine-3-carbonyl)-1H-pyrrol-3-yl]methanone (Cpd 17)

Following the protocol of Example 7 and employing pyridin-3-yl-(1,3,5-trimethyl-1H-pyrrol-2-yl)methanone hydrochloride in place of (1-methyl-1H-pyrrol-2-yl)-pyridin-3-yl-methanone hydrochloride, the title compound was obtained. Mp 85–88° C. CI-MS m/z=337 (M$^+$+H). $^1$HNMR (DMSO-d$_6$) δ 8.85–8.75 (ar, 2H); 8.3 (ar, 1H); 7.8 (ar, 3H); 7.35 (ar, 2H); 3.7 (s, 3H); 2.2 (s, 3H); 1.6 (s, 3H).

Procedure 9

(4-Chlorophenyl)-[4-(hydroxypyridin-4-yl-methyl)-1,3,5-trimethyl-1H-pyrrol-2-yl]-methanone By the method of Example 12 using 5-(4-chlorobenzoyl)-1,2,4-trimethyl-1H-pyrrole-3-carbaldehyde in place of 2-(4-chlorobenzoyl)-1-methyl-1H-pyrrole-3-carboxaldehyde gave the title compound in 47% yield. ES-MS m/z=355 (M$^+$+H).

Example 18

(4-Chlorophenyl)-[4-(hydroxypyridin-4-yl-methyl)-1,3,5-trimethyl-1H-pyrrol-2-yl]methanone (Cpd 18)

By the method of Procedure 7 substituting (4-chlorophenyl)-[4-(hydroxypyridin-4-yl-methyl)-1,3,5-trimethyl-1H-pyrrol-2-yl]-methanone for 5-[[2-(4-chlorobenzoyl)-1-methyl-1H-pyrrol-4-yl]carbonyl]-3-(triphenylmethyl)-1H-imidazolium the title compound was prepared. Treatment with ethereal HCl gave 35% yield of the hydrochloride salt. Mp. 174–176° C. ES-MS m/z=353 (M$^+$+H). $^1$HNMR (CDCl$_3$) δ 8.9 (ar, 2H); 8 (ar, 2H); 7.7 (ar, 2H); 7.5 (ar, 2H); 3.75 (s, 3H); 2.3 (s, 3H); 2.65 (s, 3H).

Example 19

(4-Chlorophenyl)-[4-(2-chloropyridine-4-carbonyl)-1-methyl-1H-pyrrol-2-yl]methanone (Cpd 19)

A solution of 3.6 g (0.010 mole) of 4-[2-(4-chlorobenzoyl)-1-methyl-1H-pyrrol-4-yl]-1-oxido-4pyridinylmethanol in 32 mL of POCl$_3$ was refluxed for 4 h. After cooling the solvent was evaporated in vacuo. The residue was taken up in CH$_2$Cl$_2$, washed with 3N NaOH, water, brine and dried (Na$_2$SO$_4$). The residue was taken up in 15 mL of EtOH and 15 mL of toluene and the water from the azeotropic mixture was refluxed off with a Dean-Stark trap for 2 h. The solvent was evaporated in vacuo. The residue was suspended in hot EtOH and the solid filtered. The solid was dissolved in MeOH with 10% CH$_2$Cl$_2$ and ethereal HCl was added. The solid was filtered to give a 24% yield of the title compound. Mp. 182–184° C. ES-MS m/z=359. $^1$HNMR (DMSO-d$_6$) δ 8.6 (ar, 1H); 8.1 (ar, 1H); 7.9–7.7 (ar, 6H); 7.1 (ar, 1H); 4.0 (s, 3H).

Biological Examples

The compounds of the present invention are useful as agents for treating or modulating a central nervous system disorder. The following biological examples demonstrate the use of the instant compounds for treating or modulating a central nervous system disorder.

The methods of the present invention include a method for treating or modulating a central nervous system disorder wherein the central nervous system disorder includes, and is not limited to, neuropathic pain, chronic pain (including chronic pain caused by inflammation or an inflammatory-related condition, osteoarthritis or rheumatoid arthritis), pain, neurological conditions (including epilepsy and bipolar disorder), cardiovascular diseases and other disorders (including functional bowel disorders), psychotic disorders, movement disorders, anxiety disorders or neurodegenerative disorders.

Neuropathic pain includes, and is not limited to, neuropathic pain resulting from chronic or debilitating conditions (such as painful diabetic peripheral neuropathy, post-herpetic neuralgia, trigeminal neuralgia, post-stroke pain, multiple sclerosis-associated pain, neuropathies-associated pain (such as in idiopathic or post-traumatic neuropathy and mononeuritis), HIV-associated neuropathic pain, cancer-associated neuropathic pain, carpal tunnel-associated neuropathic pain, spinal cord injury-associated pain, complex regional pain syndrome, fibromyalgia-associated neuropathic pain, lumbar and cervical pain, reflex sympathetic dystrophy, phantom limb syndrome and other chronic and debilitating condition-associated pain syndromes), sympathetically maintained pain or cluster and migraine headache-associated pain; pain associated with cancer, fibromyalgia, back disorders or migraine and chronic headache, adiposis dolorosa and burn pain, central pain conditions following stroke, thalamic lesions or multiple sclerosis or pain resulting from damage to the peripheral or central nervous system (after amputation, paraplegia, herpes or as a result of diabetic polyneuropathy).

Chronic pain includes, and is not limited to, chronic pain caused by inflammation or an inflammatory-related condition, osteoarthritis, rheumatoid arthritis or as sequela to disease, acute injury or trauma and includes upper back pain or lower back pain (resulting from systematic, regional or primary spine disease (such as radiculopathy), inflammation or an inflammatory-related condition), bone pain (due to osteoarthritis, osteoporosis, bone metastases or unknown reasons), pelvic pain, spinal cord injury-associated pain, cardiac chest pain, non-cardiac chest pain, central post-stroke pain, myofascial pain, cancer pain, AIDS pain, sickle cell pain, geriatric pain or pain caused by headache (such as chronic or migraine), trigeminal neuralgia, temporomandibular joint syndrome, fibromyalgia syndrome, osteoarthritis, rheumatoid arthritis, gout, fibrositis or thoracic outlet syndromes and includes use of the instant compounds as a local anesthetic for the treatment thereof.

Pain includes, and is not limited to, pain that is centrally mediated, pain that is peripherally mediated, pain that is caused by structural tissue injury, pain that is caused by soft tissue injury or pain that is caused by progressive disease, acute pain (caused by acute injury, trauma, illness, sports-medicine injuries, carpal tunnel syndrome, burns, musculoskeletal sprains and strains, musculotendinous strain, cervicobrachial pain syndromes, dyspepsia, gastric ulcer, duodenal ulcer, dysmenorrhea, endometriosis or surgery (such as open-heart or bypass surgery)), post-operative pain, kidney stone pain, gallbladder pain, gallstone pain, obstetric pain, rheumatological pain or dental pain and includes use of the instant compounds as a local anesthetic for the treatment thereof.

Neurological conditions include, and are not limited to, conditions such as anxiety, convulsions, cyclophrenia, hypotonia, epilepsy (including simple partial seizures, complex partial seizures, secondary generalised seizures and generalized seizures (further including absence seizures, myoclonic seizures, clonic seizures, tonic seizures, tonic clonic seizures and atonic seizures), bipolar disorder (such as bipolar disorder type I, bipolar disorder type II, cyclothymic disorder, rapid cycling, ultradian cycling, bipolar depression, acute mania, mania, mixed mania, hypomania and episodes associated with bipolar disorder) or unipolar depression.

Cardiovascular diseases and other disorders include, and are not limited to, arrhythmias (including cardiac arrhythmia, cardiac infarction or angina pectoris), hypertension, endocrine disorders (such as acromegaly or diabetes insipidus), tinnitus, muscle spasm, urinary incontinence, diarrhea, pruritus, functional bowel disorders (such as non-ulcer dyspepsia, non-cardiac chest pain or irritable bowel syndrome), muscular sclerosis, macular degeneration or glaucoma, diseases in which the pathophysiology of the disorder involves excessive or hypersecretory or otherwise inappropriate cellular secretion of an endogenous substance (such as a catecholamine, a hormone or a growth factor) or emesis.

Psychotic disorders include, and are not limited to, schizophrenia (including paranoid schizophrenia, hebephrenic schizophrenia, catatonic schizophrenia, undifferentiated schizophrenia, post-schizophrenic depression, residual schizophrenia, simple schizophrenia or unspecified schizophrenia), schizophreniform disorder, schizoaffective disorder, delusional disorder, brief psychotic disorder, shared psychotic disorder, psychotic disorder due to a general medical condition, substance-induced psychotic disorder or a psychotic disorder not otherwise specified.

Movement disorders include, and are not limited to, benign essential tremor, tremor in Parkinson's disease, Parkinsonism tremor, other non-related essential or Parkinsonism tremors (such as central tremors or non-classic tremors (including head/limb resting tremor, simple kinetic tremor, intention tremor, orthostatic tremor, enhanced physiologic tremor, psychogenic tremor, cerebellar tremor, rubral tremor or tremors associated with posture, position, voice or task) or drug-induced tremors and movement disorders (such as postural tremor, acute dystonia, chorea, akathisia, tardive dyskinesia or Parkinson's-like syndromes)), restless leg syndrome, restless arm syndrome, chorea in Huntington's disease, tremors associated with multiple sclerosis or Gilles de La Tourette's syndrome, post-spinal cord injury spasms, post-anoxic spasms, idiopathic torsion dystonia, focal torsion dystonia, myoclonus, athetosis, paroxysmal movement disorders (such as paroxystic dystony, paroxystic ataxia or paroxystic tremors) or abnormal movements (such as Wilson's disease).

Anxiety disorders include, and are not limited to, generalized anxiety disorder, panic disorders (such as agoraphobia, panic disorders without agoraphobia, anticipatory anxiety, recurrent sleep panic attacks, distressing symptoms (such as dyspnea, tachycardia, palpitations, headaches, dizziness, paresthesias, choking, smothering feeling, nausea or bloating) or feelings of impending doom); impulse control disorders (such as obsessive-compulsive disorder, bulimia, episodic dyscontrol, trichotillomania, compulsive gambling and kleptomania); phobic disorders (such as from social phobia, global social phobia, specific social phobia, simple phobia, agoraphobia, apiphobia, tropophobia, astrapophobia, triskaidekaphobia, blennophobia, thalassophobia, claustrophobia, spheksophobia, cynophobia, sciophobia, decidophobia, eletrophobia, scholionophobia, eremophobia, pyrophobia, gamophobia, pnigerophobia, ophidiophobia, odynophobia, nyctophobia, ochlophobia, musophobia, keraunophobia, katagelophobia, kakorraphiophobia, hydrophobia, gynophobia, gatophobia, gephyrophobia, acrophobia or amathophobia); posttraumatic stress disorder, dissociative states (such as amnesia, somnambulism, dissociative identity disorder or depersonalization), presurgical anxiety states, postsurgical anxiety states or other medical or psychiatric induced anxiety conditions (such as anxiety resulting from traumatic brain injury, chronic pain disorders or other chronic disease conditions.

Neurodegenerative disorders include, and are not limited to, acute neurodegenerative disorders (such as those associated with an abrupt insult resulting from acute injury (such as brain trauma, focal brain trauma, diffuse brain damage, spinal cord injury, intracranial lesions (including contusion, penetration, shear, compression or laceration lesions), intravertebral lesions (including contusion, penetration, shear, compression or laceration lesions) or whiplash shaken infant syndrome), anoxic ischemia, hypoxic ischemia, hypoglycemic ischemia (where the ischemia is a result of cerebrovascular insufficiency, cerebral ischemia or infarction (originating from edema, embolic occlusion, thrombotic occlusion, reperfusion following acute ischemia, perinatal hypoxic-ischemic or asphyxia injury, cardiac arrhythmia, ischemia, spasm or arrest or intracranial hemorrhage (such as epidural, subdural, subarachnoid or intracerebral hemorrhage)), drowning or carbon monoxide poisoning) or the combination thereof resulting in neuronal cell death or compromise); chronic neurodegenerative disorders (such as those associated with progressive neuronal cell death or compromise over a period of time (including Alzheimer's disease, Pick's disease, diffuse Lewy body disease, progressive supranuclear palsy (such as Steel-Richardson syndrome), multisystem degeneration (such as Shy-Drager syndrome), chronic epileptic conditions associated with neurodegeneration, motor neuron diseases (such as amyotrophic lateral sclerosis (ALS)), multiple sclerosis, degenerative ataxias, cortical basal degeneration, ALS-Parkinson's-Dementia complex of Guam, HIV-induced dementia and blindness, subacute sclerosing panencephalitis, Huntington's disease, Parkinson's disease, Down's Syndrome, Korsakoff's disease, synucleinopathies (such as multiple system atrophy), primary progressive aphasia, striatonigral degeneration, Machado-Joseph disease/spinocerebellar ataxia type 3 and olivopontocerebellar atrophy or degeneration, Gilles De La Tourette's disease, bulbar and pseudobulbar palsy, spinal and spinobulbar muscular atrophy (such as Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohifart-Kugelberg-Welander disease, spastic paraparesis, progressive multifocal leukoencephalopathy, familial dysautonomia (such as Riley-Day syndrome) or prion diseases (such as Creutzfeldt-Jakob disease, Gerstmann-Sträussler-Scheinker disease, Kuru disease or fatal familial insomnia)); other acute or chronic neurodegenerative disorders associated with memory loss (as a result of age-related dementia, vascular dementia, multi-infarct dementia, diffuse white matter disease (such as Binswanger's disease), dementia of endocrine or metabolic origin, dementia of head trauma or diffuse brain damage, dementia pugilistica or frontal lobe dementia); or, other acute or chronic neurodegenerative disorders associated with neuronal injury (such as those associated with chemical, toxic, infectious and radiation injury of the nervous system, injury during fetal development, prematurity at time of birth, anoxic-ischemia, injury from hepatic, glycemic, uremic, electrolyte and endocrine origin, injury of psychiatric origin (as a result of psychopathology, depression or anxiety), injury from peripheral diseases and plexopathy (such as plexus palsies); and, injury from neuropathy (as a result of multifocal, sensory, motor, sensory-motor, autonomic, sensory-autonomic or demyelinating neuropathies (such as Guillain-Barre syndrome or chronic inflammatory demyelinating polyradiculoneuropathy), from neuropathies originating from infections, inflammation, immune disorders, dependence/tolerance/reverse tolerance to a dependence-inducing agent (such as alcohol, opioids, CNS depressants, psychostimulants or nicotine), pharmacological treatments, toxins, trauma (such as compression, crush, laceration or segmentation traumas), metabolic disorders (such as endocrine or paraneoplastic), Charcot-Marie-Tooth disease (such as type 1a, 1b, 2, 4a or 1-X linked), Friedreich's ataxia, metachromatic leukodystrophy, Refsum's disease, adrenomyeloneuropathy, Ataxia-telangiectasia, Dejerine-Sottas (type A or B), Lambert-Eaton syndrome or disorders of the cranial nerves), from peripheral neuropathies (such as trigeminal neuralgia, postherpetic neuralgia, diabetic neuropathy, glossopharyngeal neuralgia, lumbar and cervical radiculopathies, reflex sympathetic dystrophy and causalgia) or from neuropathy secondary to metastatic infiltration); neuronal loss (associated with stroke, global and focal ischemia, CNS trauma, hypoglycemia, surgery and spinal cord trauma) and includes use of the instant compounds as neuroprotective agents (treating neurodegeneration following stroke, cardiac arrest, pulmonary bypass, traumatic brain injury and spinal cord injury.

Biological Example 1
Screening Assay for Voltage-Gated Sodium Channel Antagonists Fluorometric Membrane Potential Assay The activity of the present compounds as sodium channel modulating agents was demonstrated by the fluorometric membrane potential assay in SK-N-SH cells as described below.

Procedure

SK-N-SH neuroblastoma cells were maintained in a propagation medium containing modified Eagle's medium and 10% (v/v) fetal bovine serum and were incubated at 37° C. in a 5% $CO_2$ atmosphere. Only cells with fewer than 20 passages were used in each assay. All drugs were prepared in DMSO, and the final concentration of solvent was less than 0.1% (v/v). Veratridine, a toxin that selectively promotes persistent activation of voltage-gated sodium channels, served as the stimulus. 24 hr prior to testing, $1\times10^5$ cells/well were plated into 96-well plates specifically designed for use in a fluorescent imaging plate reader (FLIPR) (Molecular Devices, Sunnyvale, Calif.)

Prior to screening, monolayers of cells were loaded with 100 $\mu$L/well of a proprietary voltage-sensitive dye (Molecular Devices, Sunnyvale, Calif.) for 30 min at 37° C. After this incubation period, the cells were stimulated with 5 $\mu$M veratridine in the presence or absence of investigational compounds (prepared at a final concentration of 10 $\mu$M in DMSO). A sample containing 5 $\mu$M veratridine and 10 $\mu$M tetrodotoxin accounted for nonspecific activity. The fluorescence was monitored by the FLIPR (Molecular Devices) from 10 sec prior to drug addition (50 $\mu$L) to 170 sec after drug addition at 25° C. During sodium channel activation, the cells depolarize and the dye associates with cell membranes, resulting in increased fluorescence.

Analysis

As shown in Table 3, the % fluorescence inhibition (% FI) in the membrane by a compound tested was calculated according to the formula:

$$\%FI=100\times[1-[(TCF-NSF)/(CCF-NSF)]];$$

wherein FTC is defined as Test Compound Fluorescence, CCF is Control Compound Fluorescence (where 5 $\mu$M veratridine was used as the control) and NSF is Non-Specific-Fluorescence.

TABLE 3

| Cpd | % FI at 10 $\mu$M |
|---|---|
| 1 | 32 |
| 2 | 76 |
| 3 | 45 |
| 4 | 49 |
| 5 | 26 |
| 6 | 25 |
| 7 | 45 |
| 8 | 67 |
| 9 | 26 |
| 10 | 60 |
| 11 | 39 |
| 12 | 60 |
| 13 | 62 |
| 14 | 54 |
| 15 | 40 |
| 16 | 29 |
| 17 | 15 |

The results of the fluorometric membrane potential assay suggest that compounds of the present invention may be effective in treating or modulating a central nervous system disorder.

For treating or modulating a central nervous system disorder, a compound selected from Formula (I) or Formula (II) may be employed at a daily dosage in the range of from about 30 to about 4000 mg, usually in 2 to 4 divided doses, for an average adult human. A unit dose would contain from about 10 to about 500 mg of the active ingredient. More generally, for mammals, the treatment would comprise the daily administration of from about 0.001 mg/kg to about 500 mg/kg.

In particular, a pharmaceutical composition of the present invention comprising a pharmaceutically acceptable carrier and a compound selected from Formula (I) or Formula (II) administered orally may be especially suitable for use in treating or modulating a central nervous system disorder.

The present invention includes a method for treating or modulating a central nervous system disorder comprising internally administering to a subject in need thereof a therapeutically effective amount of a compound selected from Formula (I) or Formula (II) or a pharmaceutical composition thereof.

Biological Example 2
Screening Assay for Voltage-Gated Sodium Channel Antagonists [$^{14}$C] Guanidinium Flux Assay The activity of the present compounds as sodium channel modulating agents was demonstrated by the [$^{14}$C] guanidinium flux assay in SK-N-SH cells as described below.

Procedure

SK-N-SH neuroblastoma cells were maintained in a propagation medium containing modified Eagle's medium and 10% (v/v) fetal bovine serum and were incubated at 37° C. in a 5% $CO_2$ atmosphere. Only cells with fewer than 20 passages were used in each assay. All drugs were prepared in DMSO, and the final concentration of solvent was less than 0.1% (v/v). Veratridine, a toxin that selectively promotes persistent activation of voltage-gated sodium channels, served as the stimulus.

SK-N-SH cells were plated at $1\times10^5$ cells/well in 96-well Cytostar-T microscintillating plates in propagation medium and experiments were performed 6–7 days after plating. Prior to assay, the SK-N-SH cells were washed twice with assay buffer containing 50 mM HEPES (pH 7.45), 5.4 mM potassium chloride, 0.8 mM magnesium chloride, 130 mM choline chloride, 5.5 mM glucose and 0.1 mg/mL bovine serum albumin. Next, the plates were allowed to equilibrate for 10 min at 37° C. in assay buffer. After this incubation period, the cells were stimulated with 100 μM veratridine in the presence or absence of investigational compounds prepared in a 96-well plate (prepared at a final concentration of 10 μM in DMSO). The 96-well dosing plate was prepared by mixing 25 μL of a drug/assay buffer solution per well with 25 μL of 0.7 μCi/mL [$^{14}$C]guanidine hydrochloride in assay buffer. 50 μL aliquots from the dosing plate were then added to the cells. One sample containing 100 μM veratridine and 10 μM tetrodotoxin accounted for nonspecific activity. The plates were incubated for 1 hr at room temperature and the radioactivity was counted in a 1450 Microbeta scintillation counter.

Analysis

As shown in Table 4, the % guanidinium flux inhibition (% GFI) by a compound tested was calculated according to the formula:

$$\%GFI=100\times[1-[(TCC-NSC)/(CCC-NSC)]];$$

wherein TCC is defined as Test Compound Counts (per minute), CCC is Control Compound Counts (per minute; 100 μM veratridine was used as the control) and NCS is Non-specific Counts (per minute).

TABLE 4

| Cpd | % GFI at 10 μM |
|---|---|
| 1 | 23 |
| 5 | 55 |
| 6 | 74 |
| 7 | 57 |
| 8 | 82 |
| 9 | 31 |
| 10 | 46 |
| 12 | 4 @ 100 μM |
| 13 | 24 |
| 14 | 14 |
| 15 | 4 |

The results of the guanidinium flux assay suggest that compounds of the present invention may be effective in treating or modulating a central nervous system disorder.

For treating or modulating a central nervous system disorder, a compound selected from Formula (I) or Formula (II) may be employed at a daily dosage in the range of from about 30 to about 4000 mg, usually in 2 to 4 divided doses, for an average adult human. A unit dose would contain from about 10 to about 500 mg of the active ingredient. More generally, for mammals, the treatment would comprise the daily administration of from about 0.001 mg/kg to about 500 mg/kg.

In particular, a pharrmaceutical composition of the present invention comprising a pharmaceutically acceptable carrier and a compound selected from Formula (I) or Formula (II) administered orally may be especially suitable for use in treating or modulating a central nervous system disorder.

The present invention includes a method for treating or modulating a central nervous system disorder comprising internally administering to a subject in need thereof a therapeutically effective amount of a compound selected from Formula (I) or Formula (II) or a pharmaceutical composition thereof.

Biological Example 3
Procedure for Testing in Mouse Anticonvulsant Model

The activity of the present compounds as anticonvulsant agents was determined using a standard mouse "maximal electroshock test" (MES). In this test, activity was indicated by a block of the toxic extensor seizure, as described by Swinyard, et al. (J. Pharmacol. Exptl. Therap., 1952, 106, 319). A more recent description of current anticonvulsant drug screening is given in Swinyard, et al., in Epilepsia, 1978, 19, 409.

The anticonvulsant activity of the instant compounds is shown in Table 5 and was evaluated according to the Swinyard (1952) method. The abbreviations used in the table have the following meanings: mpk refers to the dose orally administered in "mg per Kg;" and, $ED_{50}$ refers to the "50% Effective Dose" orally administered in mpk. The values marked by an * represent the number of mice protected/number of mice tested; therefore, a value of 3/3 represents that the number of mice protected matched the number of mice tested at the indicated dose.

TABLE 5

| Cpd | MES Response |
|---|---|
| 1 | $ED_{50}$ = 156.97 mpk |
| 3 | 3/3* @ 100 mpk |
| 4 | 0/1* @ 300 mpk |
| 6 | 1/1* @ 30 mpk |
| 7 | 2/3* @ 100 mpk |
| 8 | 0/1* @ 300 mpk |
| 10 | 0/1* @ 300 mpk |
| 11 | 0/1* @ 300 mpk |

The results of the mouse MES model suggest that compounds of the present invention may be effective in treating epilepsy or in modulating the symptoms thereof.

For treating epilepsy or modulating the symptoms thereof, a compound selected from Formula (I) or Formula (II) should not have A selected from 2-naphthalenylcarbonyl attached to the pyrrole ring on the 4 position or, independently, should not have B selected from 2-thienylcarbonyl, 2-pyridinylcarbonyl or 4-pyridinylcarbonyl attached to the pyrrole ring on the 2 position.

For treating epilepsy or modulating the symptoms thereof, a compound selected from Formula (I) or Formula (II) may be employed at a daily dosage in the range of from about 30 to about 4000 mg, usually in 2 to 4 divided doses, for an average adult human. A unit dose would contain from about 10 to about 500 mg of the active ingredient. More generally, for mammals, the treatment would comprise the daily administration of from about 0.001 mg/kg to about 50 mg/kg.

A compound selected from Formula (I) or Formula (II) may be used in treating epilepsy or in modulating the symptoms thereof in a manner similar to that used for phenytoin. Medical aspects of the treatment of epilepsy are described in L. S. Goodman, et. al., in "The Pharmacological Basis of Therapeutics", 5th Ed. pages 201 to 226, Macmillan (1975).

In particular, a pharmaceutical composition of the present invention comprising a pharmaceutically acceptable carrier and a compound selected from Formula (I) or Formula (II) administered orally may be especially suitable for use in treating epilepsy or in modulating the symptoms thereof.

The present invention includes a method for treating epilepsy or modulating the symptoms thereof comprising internally administering to a subject suffering from the symptoms of epilepsy a therapeutically effective amount of a compound selected from Formula (I) or Formula (II) or a pharmaceutical composition thereof.

Biological Example 4
Procedure for Testing Antiallodynic Effect

The procedure used to detect the antiallodynic effect of a compound of the present invention for which there is a good correlation with human efficacy for the treatment of pain is the procedure for the measurement of allodynia found in the Chung Model (Kim S. H. and Chung J. M., An Experimental Model for Peripheral Neuropathy Produced by Segmental Spinal Nerve Ligation in the Rat, *Pain*, 1992, 50, 355–363). The antiallodynic effect of the composition of the present invention in the Chung Model is expressed in % MPE (Maximum Possible Effect).

Male Sprague-Dawley rats, weighing approximately 200 g each were anesthetized with isoflurane. The spinal nerve at the level of $L_5$ was exposed through an incision just left of the dorsal midline and tightly ligated with 6-0 silk. At various times after surgery, animals were tested for mechanical allodynia with von Frey hairs (monofilaments which are calibrated to bend under a certain amount of pressure, ranging from 0.41 to 15.1 g). In order to calculate a paw withdrawal threshold (PWT), tactile allodynia was measured by recording the pressure at which the affected paw was withdrawn from graded stimuli according to the procedure of S. R. Chaplan, J. W. Pogrel, T. L. Yaksh, Role of Voltage-Dependent Calcium Channel Subtypes in Experimental Tactile Allodynia, *J. Pharmacol. Exp. Ther.*, 1994, 269, 1117–1123. Normal rats can withstand at least 15 g of pressure without responding. Operated rats, however, can respond to as little as 0.25 g of pressure. The surgery was deemed successful if the animal responded with a PWT of less than 4 g of pressure applied to the affected paw. Rats were included in the study only if they did not exhibit motor dysfunction (e.g., paw dragging or dropping) and their PWT was below 39.2 mN (equivalent to 4.0 g). The PWT was used to calculate the % maximal possible effect (% MPE) according to the formula:

$$\%MPE=100\times[(PWT-CT)/(CO-CT)];$$

wherein PWT is defined as Paw Withdrawal Threshold, CT is Control Threshold, and CO is Cut Off (defined as 15 g).

The sham operation consisted of a similar surgery; the spinal nerve was visualized without being ligated. These animals were also tested for mechanical allodynia and showed no response to greater than 15 g of force applied to the ipsilateral paw.

Compounds selected from Formula (I) and Formula (II) were tested for activity in treating or modulating neuropathic pain by being dissolved or suspended in either water or hydroxypropyl methylcellulose, respectively. Postoperative animals between 14 to 42 days were fasted overnight prior to dosing. Animals were orally dosed and dosage volumes were calculated on a 4 mL/kg basis.

Table 6 shows results as either the $ED_{50}$ or % MPE in the Chung Model for certain compounds selected from Formula (I) and Formula (II). The abbreviations used in the table have the following meanings: IA refers to "inactive at the screening dose;" $ED_{50}$ refers to the "50% Effective Dose" orally administered in mg per Kg (mpk).

TABLE 6

| Cpd | $ED_{50}$ or % MPE |
|---|---|
| 1 | $ED_{50}$ = 22 mpk |
| 2 | 7% |
| 3 | 5% |
| 4 | IA |
| 5 | 9% |
| 6 | 12% |
| 7 | $ED_{50}$ = 22 mpk |
| 8 | 1.3% |
| 9 | 5% |
| 10 | 11% |
| 11 | 10% |
| 12 | 3.7% |
| 13 | IA |
| 15 | 7.9% |
| 16 | $ED_{50}$ = 29 mpk |
| 17 | 59% |

The results of the "Chung Model" study suggest that antiallodynic compounds of the present invention may be effective in treating or modulating neuropathic pain.

For treating or modulating neuropathic pain, a compound selected from Formula (I) or Formula (II) should not have B selected from 2-thienylcarbonyl attached to the pyrrole ring on the 2 position or 1H-imidazol-5-ylcarbonyl attached to the pyrrole ring on the 4 position.

For treating or modulating neuropathic pain, a compound selected from Formula (I) or Formula (II) may be employed at a daily dosage in the range of from about 30 to about 4000 mg, usually in 2 to 4 divided doses, for an average adult human. A unit dose would contain from about 10 to about 500 mg of the active ingredient. More generally, for mammals, the treatment would comprise the daily administration of from about 0.001 mg/kg to about 500 mg/kg.

In particular, aa pharmaceutical composition of the present invention comprising a pharmaceutically acceptable carrier and a compound selected from Formula (I) or Formula (II) administered orally may be especially suitable for use in treating or modulating neuropathic pain.

The present invention includes a method for treating or modulating neuropathic pain comprising internally administering to a subject in need thereof a therapeutically effective amount of a compound selected from Formula (I) or Formula (II) or a pharmaceutical composition thereof.

Biological Example 5
Procedure for Testing Hyperalgesic Effect

The procedure used to detect the antihyperalgesic activity of a compound of the present invention for which there is a good correlation with human efficacy is the Carrageenan Paw Hyperalgesia Test (as described in Sammons, et al., *Brain Research*, 2000, 876, 48–54).

Animals

Male, CD-1 mice (Charles River Laboratories) weighing 22–30 g each at the time of testing are housed in a climate-controlled, virus free environment for at least 7 days prior to testing. Food and water are available ad libitum up to test time.

Animal Dosing

Test mice are immunized by injecting an irritant (e.g., 0.02 mL of a 1.0% carrageenan solution in 0.9% saline) subcutaneously into the subplantar tissue of one of the hind paws to stimulate an acute inflammatory reaction. The response of the animal following carrageenan injection is subsequently evaluated at a fixed later time and verified to be hyperalgesic relative to a baseline response obtained immediately prior to carrageenan injection.

The mice were dosed orally with either Compound 1 dissolved in a suspension of 20% hydroxypropyl beta cyclodextrin in distilled water or with vehicle alone at a fixed time following carrageenan injection. The dosing volume was 10 mL/kg. Response latencies were subsequently evaluated at fixed times following oral dosing to assess reversal of hyperalgesia caused by treatment with Compound 1 as compared to vehicle treatment.

Measurement of Hyperalgesia

Hyperalgesia is assessed by measurement of a response to a thermal stimulus. Measurement of thermal hyperalgesia is made with a standard laboratory hot plate apparatus, whose surface temperature is precisely determined and evenly maintained. Alternatively, hyperalgesia is evaluated with a commercially available Hargreaves apparatus which selectively elevates the temperature of an individual paw (Dirig, et al., J. Neurosci. Methods, 1997, 76, 183). A response is defined as any shaking, licking, or tucking of the treated paw. With either apparatus, hyperalgesia is defined as a reduced latency to response compared to the baseline latency recorded prior to carrageenan injection and the antihyperalgesic effect of the test compound is seen as a (partial) restoration of the latency toward normal (Dirig, et al., J. Pharmacol. Expt. Therap., 1998, 285, 1031).

The reversal of hyperalgesia produced by therapeutic intervention is expressed as a percent recovery (% R), that is, a percentage of the full reversal possible, taking into account individual differences in baseline response latencies and the severity of post carrageenan hyperalgesia as assessed prior to therapeutic intervention.

The % Recovery (% R) by a compound tested was calculated according to the formula:

$$\%R=100\times[(PDL-PCL)/(BL-PCL)];$$

wherein PDL is defined as Post Drug Latency, PCL is Post Carrageenan Latency and BL is Baseline Latency.

The results in the Carrageenan Paw Model for Compound 1 orally administered at 30 mg per Kg demonstrates a % Recovery of 84% compared to a vehicle control % Recovery of 12% when each group was assessed at 90 minutes following oral dosing.

The results in the Carrageenan Paw Model suggest that compounds of the present invention may be effective as antihyperalgesic agents in treating or modulating pain associated with inflammation or an inflammatory-related disorder.

For treating or modulating inflammation or an inflammatory-related disorder, a compound selected from Formula (I) or Formula (II) may be employed at a daily dosage in the range of from about 30 to about 4000 mg, usually in 2 to 4 divided doses, for an average adult human. A unit dose would contain from about 10 to about 500 mg of the active ingredient. More generally, for mammals, the treatment would comprise the daily administration of from about 0.001 mg/kg to about 500 mg/kg.

In particular, a pharmaceutical composition of the present invention comprising a pharmaceutically acceptable carrier and a compound selected from Formula (I) or Formula (II) administered orally may be especially suitable for use in treating or modulating inflammation or an inflammatory-related disorder.

The present invention includes a method for treating or modulating inflammation or an inflammatory-related disorder comprising internally administering to a subject in need thereof a therapeutically effective amount of a compound selected from Formula (I) or Formula (II) or a pharmaceutical composition thereof.

Biological Example 6
Procedure for Testing Antiinflammatory Response

The procedure used to detect the antiinflammatory activity of a compound of the present invention for which there is a good correlation with human efficacy is the Carrageenan Paw Edema Model (as described in Levy, L., Carrageenan Paw Edema in the Mouse, Life Sci., 1969, 8, 11, 601–6).

Animals

Male, Sprague-Dawley rats (Charles River Laboratories) 175–200 g are housed in a climate-controlled, virus free environment for at least 5 days prior to testing.

Procedure

Carrageenan is prepared in saline (0.5% carrageenan solution in 0.9% saline) and injected in a 0.1 mL volume into the footpad of the rat. Test compound is administered orally by gavage 30–60 minutes prior to footpad challenge. Paws are dipped into a mercury plethysmograph edema computer (Buxco Electronics) and the foot displacement is recorded at 0 time and at various times after challenge with carrageenan. Rats treated with test compound are compared to vehicle controls for any inhibition of carrageenan induced paw swelling.

The % Inhibition (% I) by a compound tested was calculated according to the formula:

$$\%I=100-[100\times(TCPV/VCPV)];$$

wherein TCPV is defined as the mean Change in Paw Volume in the Treated group and VCPV is the mean Change in Paw Volume in the Vehicle group.

Rats treated with Compound I at a dose of 100 mg/kg, p.o., exhibited a 35% inhibition of carrageenan-induced paw swelling at 2 hours post carrageenan administration. The results in the Paw Edema Model suggest that compounds of the present invention may be effective as antiinflammatory agents in treating or modulating inflammation or an inflammatory-related disorder.

For treating or modulating inflammation or an inflammatory-related disorder, a compound selected from Formula (I) or Formula (II) may be employed at a daily dosage in the range of from about 30 to about 4000 mg, usually in 2 to 4 divided doses, for an average adult human. A unit dose would contain from about 10 to about 500 mg of the active ingredient. More generally, for mammals, the treatment would comprise the daily administration of from about 0.001 mg/kg to about 500 mg/kg.

In particular, a pharmaceutical composition of the present invention comprising a pharmaceutically acceptable carrier and a compound selected from Formula (I) or Formula (II) administered orally may be especially suitable for use in treating or modulating inflammation or an inflammatory-related disorder.

The present invention includes a method for treating or modulating inflammation or an inflammatory-related disorder comprising internally administering to a subject in need thereof a therapeutically effective amount of a compound selected from Formula (I) or Formula (II) or a pharmaceutical composition thereof.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound selected from the Formula (I) or Formula (II):

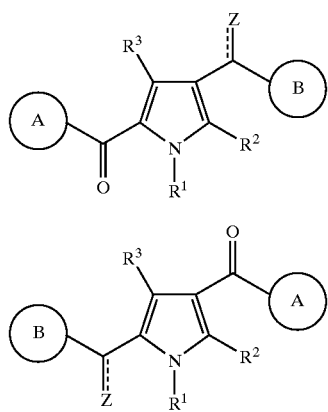

Formula (I)

Formula (II)

wherein

A is selected from the group consisting of phenyl and naphthalenyl optionally substituted with 1 to 4 substituents;

B is selected from heteroaryl optionally substituted on 1 to 4 available carbon atom ring members with a substituent selected from the group consisting of halogen, $C_{1-8}$alkyl, $C_{1-8}$alkoxy, hydroxy, hydroxy($C_{1-8}$)alkyl, hydroxy($C_{1-8}$)alkoxy, (halo)$_{1-3}$($C_{1-8}$)alkyl and (halo)$_{1-3}$ ($C_{1-8}$) alkoxy; and, optionally substituted on available nitrogen atom ring members with a substituent selected from the group consisting of $C_{1-8}$alkyl, $C_{2-8}$alkenyl, hydroxy($C_{1-8}$)alkyl, (halo)$_{1-3}$($C_{1-8}$)alkyl and oxido;

Z is selected from the group consisting of oxo and hydroxy;

$R^1$ is selected from the group consisting of:

$C_{1-8}$alkyl {wherein alkyl is optionally substituted on a terminal carbon with one substituent selected from the group consisting of $C_{1-8}$alkoxy, —C(O)— (substituted with one substituent selected from the group consisting of H, OH, $C_{1-8}$alkyl, $C_{1-8}$alkoxy, $NH_2$, —NH($C_{1-8}$) alkyl, —N(($C_{1-8}$)alkyl)$_2$), —NHC(O)— (substituted with one substituent selected from the group consisting of H, OH, $C_{1-8}$alkyl, $C_{1-8}$alkoxy, $NH_2$, —NH($C_{1-8}$) alkyl, —N(($C_{1-8}$)alkyl)$_2$), —OC(O)— (substituted with one substituent selected from the group consisting of H, OH, $C_{1-8}$alkyl, $C_{1-8}$alkoxy, $NH_2$, —NH($C_{1-8}$)alkyl, —N(($C_{1-8}$)alkyl)$_2$), $NH_2$, —NH($C_{1-8}$)alkyl, —N(($C_{1-8}$) alkyl)$_2$, —S($C_{1-8}$)alkyl, —SO$_2$($C_{1-8}$)alkyl, cyano, (halo)$_{1-3}$; hydroxy and nitro}, cycloalkyl and aryl {wherein cycloalkyl and aryl are optionally substituted with 1 to 4 substituents independently selected from the group consisting of cyano, halo, hydroxy and nitro; and, wherein cycloalkyl and aryl are optionally substituted with one substituent selected from the group consisting of $C_{1-8}$alkyl, (wherein alkyl is optionally substituted on a terminal carbon with one substituent selected from the group consisting of $NH_2$, —NH($C_{1-8}$)alkyl, —N(($C_{1-8}$)alkyl)$_2$, cyano, (halo)$_{1-3}$, hydroxy and nitro), $C_{1-8}$alkoxy, $NH_2$, —NH($C_{1-8}$)alkyl and —N(($C_{1-8}$) alkyl)$_2$};

$R^2$ and $R^3$ are independently selected from the group consisting of hydrogen, $C_{1-8}$alkyl and halogen;

or a pharmaceutically acceptable acid addition salt, a quaternary ammonium salt or a N-oxides thereof.

2. The compound of claim 1 wherein the aryl of A is phenyl optionally substituted with 1 to 4 substituents.

3. A compound selected from Formula (I) or Formula (II):

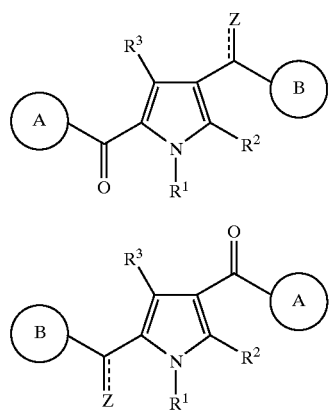

Formula (I)

Formula (II)

wherein

A is selected from the group consisting of thienyl, pyridinyl, quinolinyl and isoquinolinyl optionally substituted on 1 to 4 available carbon atom ring members with a substituent and optionally substituted on available nitrogen atom ring members with a substituent;

B is selected from heteroaryl optionally substituted on 1 to 4 available carbon atom ring members with a substituent selected from the group consisting of halogen, $C_{1-8}$alkyl, $C_{1-8}$alkoxy, hydroxy, hydroxy($C_{1-8}$)alkyl, hydroxy($C_{1-8}$)alkoxy, (halo)$_{1-3}$($C_{1-8}$)alkyl and (halo)$_{1-3}$ ($C_{1-8}$) alkoxy; and, optionally substituted on available nitrogen atom ring members with a substituent selected from the group consisting of $C_{1-8}$alkyl, $C_{2-8}$alkenyl, hydroxy($C_{1-8}$)alkyl, (halo)$_{1-3}$($C_{1-8}$)alkyl and oxido;

Z is selected from the group consisting of oxo and hydroxy;

$R^1$ is selected from the group consisting of:

$C_{1-8}$alkyl {wherein alkyl is optionally substituted on a terminal carbon with one substituent selected from the group consisting of $C_{1-8}$alkoxy, —C(O)— (substituted with one substituent selected from the group consisting of H, OH, $C_{1-8}$alkyl, $C_{1-8}$alkoxy, $NH_2$, —NH($C_{1-8}$) alkyl, —N(($C_{1-8}$)alkyl)$_2$), —NHC(O)— (substituted with one substituent selected from the group consisting of H, OH, $C_{1-8}$alkyl, $C_{1-8}$alkoxy, $NH_2$, —NH($C_{1-8}$) alkyl, —N(($C_{1-8}$)alkyl)$_2$), —OC(O)— (substituted with one substituent selected from the group consisting of H, OH, $C_{1-8}$alkyl, $C_{1-8}$alkoxy, $NH_2$, —NH($C_{1-8}$)alkyl, —N(($C_{1-8}$)alkyl)$_2$), $NH_2$, —NH($C_{1-8}$)alkyl, —N(($C_{1-8}$) alkyl)$_2$, —S($C_{1-8}$)alkyl, —SO$_2$($C_{1-8}$)alkyl, cyano, (halo)$_{1-3}$hydroxy and nitro}, cycloalkyl and aryl {wherein cycloalkyl and aryl are optionally substituted with 1 to 4 substituents independently selected from the group consisting of cyano, halo, hydroxy and nitro; and, wherein cycloalkyl and aryl are optionally substituted with one substituent selected from the group consisting of $C_{1-8}$alkyl, (wherein alkyl is optionally substituted on a terminal carbon with one substituent selected from the group consisting of $NH_2$, $-NH(C_{1-8})$alkyl, $-N((C_{1-8})$alkyl$)_2$, cyano, (halo)$_{1-3}$, hydroxy and nitro), $C_{1-8}$alkoxy, $NH_2$, $-NH(C_{1-8})$alkyl and $-N((C_{1-8})$alkyl$)_2$};

$R^2$ and $R^3$ are independently selected from the group consisting of hydrogen, $C_{1-8}$alkyl and halogen;

or a pharmaceutically acceptable acid addition salt, a quaternary ammonium salt or a N-oxides thereof.

4. The compound of claim 3 wherein the heteroaryl of A is selected from the group consisting of thienyl and pyridinyl optionally substitute on 1 to 4 available carbon atom ring members with a substituent and optionally substituted on available nitrogen atom ring members with a substituent.

5. A compound selected from Formula (I) or Formula (II):

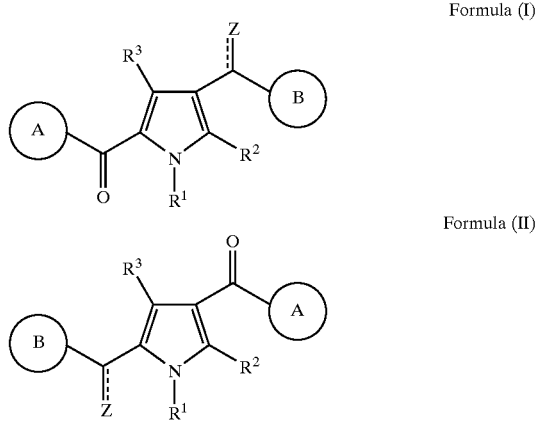

Formula (I)

Formula (II)

wherein

A is selected from the group consisting of aryl (optionally substituted with 1 to 4 substituents independently selected from the group consisting of halogen, $C_{1-8}$alkyl, $C_{1-8}$alkoxy, hydroxy, hydroxy($C_{1-8}$)alkyl, hydroxy($C_{1-8}$)alkoxy, (halo)$_{1-3}$($C_{1-8}$)alkyl and (halo)$_{1-3}$($C_{1-8}$)alkoxy and heteroaryl (optionally substituted on 1 to 4 available carbon atom ring members with a substituent selected from the group consisting of halogen, $C_{1-8}$alkyl, $C_{1-8}$alkoxy, hydroxy, hydroxy($C_{1-8}$)alkyl, hydroxy($C_{1-8}$)alkoxy, (halo)$_{1-3}$($C_{1-8}$)alkyl and (halo)$_{1-3}$($C_{1-8}$)alkoxy; and optionally substituted on available nitrogen atom ring members with a substituent selected from the group consisting of $C_{1-8}$alkyl, hydroxy($C_{1-8}$)alkyl and (halo)$_{1-3}$($C_{1-8}$)alkyl);

B is selected from the group consisting of furyl, thienyl, pyrrolyl, imidazolyl, pyridinyl, quinolinyl and isoquinolinyl optionally substituted on 1 to 4 available carbon ring members as described above for the heteroaryl in the definition of A, and optionally substituted on the available nitrogen atom ring members, with a substituent as described above for the heteroaryl in the definition of A;

Z is selected from the group consisting of oxo and hydroxy;

$R^1$ is selected from the group consisting of:

$C_{1-8}$alkyl {wherein alkyl is optionally substituted on a terminal carbon with one substituent selected from the group consisting of $C_{1-8}$alkoxy, $-C(O)-$ (substituted with one substituent selected from the group consisting of H, OH, $C_{1-8}$alkyl, $C_{1-8}$alkoxy, $NH_2$, $-NH(C_{1-8})$alkyl, $-N((C_{1-8})$alkyl$)_2$), $-NHC(O)-$ (substituted with one substituent selected from the group consisting of H, OH, $C_{1-8}$alkyl, $C_{1-8}$alkoxy, $NH_2$, $-NH(C_{1-8})$alkyl, $-N((C_{1-8})$alkyl$)_2$), $-OC(O)-$ (substituted with one substituent selected from the group consisting of H, OH, $C_{1-8}$alkyl, $C_{1-8}$alkoxy, $NH_2$, $-NH(C_{1-8})$alkyl, $-N((C_{1-8})$alkyl$)_2$), $NH_2$, $-NH(C_{1-8})$alkyl, $-N((C_{1-8})$alkyl$)_2$, $-S(C_{1-8})$alkyl, $-SO_2(C_{1-8})$alkyl, cyano, (halo)$_{1-3}$hydroxy and nitro}, cycloalkyl and aryl {wherein cycloalkyl and aryl are optionally substituted with 1 to 4 substituents independently selected from the group consisting of cyano, halo, hydroxy and nitro; and, wherein cycloalkyl and aryl are optionally substituted with one substituent selected from the group consisting of $C_{1-8}$alkyl, (wherein alkyl is optionally substituted on a terminal carbon with one substituent selected from the group consisting of $NH_2$, $-NH(C_{1-8})$alkyl, $-N((C_{1-8})$alkyl$)_2$, cyano, (halo)$_{1-3}$, hydroxy and nitro), $C_{1-8}$alkoxy, $NH_2$, $-NH(C_{1-8})$alkyl and $-N((C_{1-8})$alkyl$)_2$};

$R^2$ and $R^3$ are independently selected from the group consisting of hydrogen, $C_{1-8}$alkyl and halogen;

or a pharmaceutically acceptable acid addition salt, a quaternary ammonium salt or a N-oxides thereof.

6. The compound of claim 5 wherein the heteroaryl of B is selected from the group consisting of thienyl, imidazolyl and pyridinyl optionally substituted on 1 to 4 available carbon atom ring members with a substituent, as previously described; and, optionally substituted on available nitrogen atom ring members with a substituent.

7. A compound selected from Formula (I):

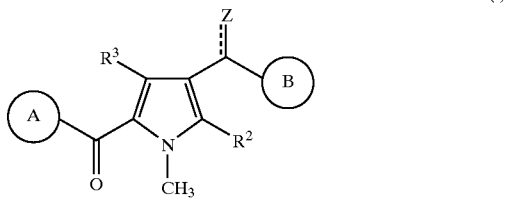

Formula (I)

wherein A, B, Z, $R^2$ and $R^3$ are dependently selected from the group consisting of:

| A | B | Z | $R^2$ | $R^3$ |
|---|---|---|---|---|
| 4-Cl—Ph | 4-pyridinyl | O | H | H; |
| Ph | 4-pyridinyl | O | H | H; |
| 4-Me—Ph | 4-pyridinyl | O | H | H; |
| 4-Cl—Ph | 4-pyridinyl | O | H | H; |
| 4-Cl—Ph | 2-pyridinyl | O | H | H; |
| 4-Cl—Ph | 4-pyridinyl | OH | H | H; |
| 4-Cl—Ph | 1H-imidazol-5-yl | O | H | H; |
| 4-Cl—Ph | 1-Me-4-pyridinyl | O | H | H; |
| 4-Cl—Ph | 1-oxido-4-pyridinyl | O | H | H; |
| 4-Cl—Ph | 1-oxido-4-pyridinyl | OH | H | H; |
| 4-Cl—Ph | 4-pyridinyl | OH | $CH_3$ | $CH_3$; |
| and, | | | | |
| 4-Cl—Ph | 2-Cl-4-pyridinyl | O | H | H. |

8. A compound selected from Formula (II):

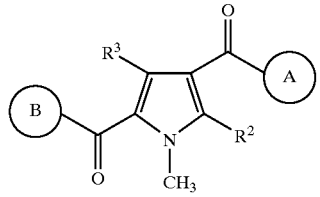

Formula (II)

wherein B, A, R² and R³ are dependently selected from the group consisting of:

| B | A | R² | R³ |
|---|---|---|---|
| 2-thienyl | 4-pyridinyl | H | H; |
| 3-pyridinyl | 4-F—Ph | H | H; |
| 3-pyridinyl | 2-naphthalenyl | H | H; |
| 6-Cl-3-pyridinyl | 4-Cl—Ph | H | H; |

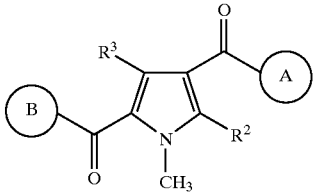

Formula (II)

wherein B, A, R² and R³ are dependently selected from the group consisting of:

| B | A | R² | R³ |
|---|---|---|---|
| 2-pyridinyl | 4-F—Ph | H | H; |
| 4-pyridinyl and, | 4-F—Ph | H | H; |
| 3-pyridinyl | 4-F—Ph | CH₃ | CH₃. |

9. A compound selected from the group consisting of:
[5-(4-Chlorobenzoyl )-1-methyl-1H-pyrrol-3-yl]pyridin-4-ylmethanone;
(4-Fluorophenyl)-[1-methyl-5-(pyridine-3-carbonyl)-1H-pyrrol-3-yl]methanone Hydrochloride; and,
(4-Chlorophenyl )-{4-[hydroxy-(1-oxy-pyridin-4-yl )methyl]-1-methyl-1H-pyrrol-2-yl}methanone.

* * * * *